United States Patent [19]

Wilson et al.

[11] Patent Number: 5,541,349

[45] Date of Patent: Jul. 30, 1996

[54] METAL COMPLEXES CONTAINING PARTIALLY DELOCALIZED II-BOUND GROUPS AND ADDITION POLYMERIZATION CATALYSTS THEREFROM

[75] Inventors: David R. Wilson; David R. Neithamer; Peter N. Nickias, all of Midland; W. Jack Kruper, Jr., Sanford, all of Mich.

[73] Assignee: The Dow Chemical Company, Midland, Mich.

[21] Appl. No.: 304,301

[22] Filed: Sep. 12, 1994

[51] Int. Cl.$^6$ ............................... C07F 5/02; C07F 7/10
[52] U.S. Cl. ............................ 556/10; 556/7; 556/13; 556/52; 502/117; 502/155; 526/160
[58] Field of Search ..................... 556/12, 52, 7, 556/10, 13; 502/117, 155; 526/160

[56] References Cited

U.S. PATENT DOCUMENTS

| | | | |
|---|---|---|---|
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,153,157 | 10/1992 | Hlatky et al. | 502/117 |
| 5,296,433 | 3/1994 | Siedle et al. | 502/117 |
| 5,321,106 | 6/1994 | LaPointe | 526/126 |

FOREIGN PATENT DOCUMENTS

| | | |
|---|---|---|
| 277003 | 8/1988 | European Pat. Off. . |
| 416815 | 3/1990 | European Pat. Off. . |
| 468651 | 1/1992 | European Pat. Off. . |
| 514828 | 11/1992 | European Pat. Off. . |
| 520732 | 12/1992 | European Pat. Off. . |
| WO9308199 | 4/1993 | WIPO . |
| WO9319104 | 9/1993 | WIPO . |
| WO9323412 | 11/1993 | WIPO . |
| WO9400500 | 1/1994 | WIPO . |
| WO9417112 | 8/1994 | WIPO . |

OTHER PUBLICATIONS

*J. Chem. Soc. Chem. Comm.*, 1993, 383–384.

Lambert, J. B., et al., *Organometallics*, 1994, 13, 2430–2443.

*J. Am. Chem. Soc.*, 1978, 100, 3258.

R. D. Ernst, *Chem Rev.* 88, 1255–1291 (1988).

R. D. Ernst, et al., *J. Am. Chem. Soc.*, 107, 5016–5018 (1985).

Jutzi, et al., *Chem. Ber.*, 117, 1885–95 (1984).

*J. Am. Chem. Soc.*, 103, 6788–6789 (1981).

*Zh. Oshch. Khim.*, 44, 226–227 (1979).

*Primary Examiner*—David W. Wu

[57] ABSTRACT

Novel Group 4 metal complexes wherein the metal is in the +2 or +4 formal oxidation state containing a cyclic or noncyclic, non-aromatic, anionic, dienyl ligand group bound to M and having a bridged ligand structure, catalytic derivatives of such complexes including novel zwitterionic complexes; and the use thereof as catalysts for polymerizing addition polymerizable monomers are disclosed.

12 Claims, No Drawings

METAL COMPLEXES CONTAINING PARTIALLY DELOCALIZED Π-BOUND GROUPS AND ADDITION POLYMERIZATION CATALYSTS THEREFROM

BACKGROUND OF THE INVENTION

This invention relates to certain Group 4 metal complexes comprising a cyclic, or noncyclic, non-aromatic, anionic, dienyl group wherein the metal of said complexes is in the +2 or +4 formal oxidation state and further wherein the metal is also covalently bonded via a second ligand group to the cyclic or noncyclic, non-aromatic, anionic, dienyl ligand group. The invention also relates to techniques for preparing such complexes, catalyst systems comprising such complexes that are useful for polymerizing addition polymerizable monomers, and to such polymerization processes themselves.

Metal complexes containing delocalized, n-bonded ligand groups and methods for their preparation are disclosed in U.S. application Ser. No. 545,403, filed Jul. 3, 1990 (EP-A-416,815); U.S. application Ser. No. 547,718, filed Jul. 3, 1990 now abn (EP-A-468,651); U.S. application Ser. No. 702,475, filed May 20, 1991 now abn (EP-A-514,828); U.S. application Ser. No. 876,268, filed May 1, 1992, (EP-A-520, 732) and U.S. application Ser. No. 8,003, filed Jan. 21, 1993 now U.S. Pat. No. 5,374,696 (WO93/19104), as well as U.S. Pat. No. 5,055,438, U.S. Pat. No. 5,057,475, U.S. Pat. No. 5,096,867, U.S. Pat. No. 5,064,802 and U.S. Pat. No. 5,132,380. The teachings of all the foregoing patents, publications and patent applications are hereby incorporated by reference.

Despite the advance in the art brought about by the foregoing metal complexes, new and improved catalytic compounds are still desired.

SUMMARY OF THE INVENTION

According to the present invention there are provided metal complexes corresponding to the formula:

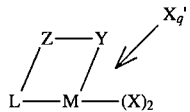

wherein:

M is a Group 4 metal in the +2 or +4 formal oxidation state;

L is a group containing a cyclic or noncyclic, non-aromatic, anionic, dienyl ligand group bound to M and Z, said L group containing up to 60 nonhydrogen atoms;

Z is a moiety covalently bound to both L and Y, comprising boron, or a member of Group 14 of the Periodic Table of the Elements, said moiety having up to 60 non-hydrogen atoms;

Y is a moiety comprising nitrogen, phosphorus, sulfur or oxygen through which Y is covalently bound to both Z and M, said moiety having up to 20 nonhydrogen atoms;

X' independently each occurrence is a Lewis base containing up to 40 nonhydrogen atoms;

X independently each occurrence is a monovalent anionic moiety having up to 20 non-hydrogen atoms, provided however that neither X is an aromatic group that is n-bonded to M; optionally, two X groups may be covalently bound together forming a divalent dianionic moiety having both valences bound to M; or two X groups together form a neutral, conjugated or nonconjugated diene that is n-bonded to M (whereupon M is in the +2 oxidation state); or further optionally one or more X and one or more X' groups may be bonded together thereby forming a moiety that is both covalently bound to M and coordinated thereto by means of Lewis base functionality; and q is a number from 0 to 3.

Additionally according to the present invention there are provided processes for preparing such complexes comprising contacting a precursor Group 4 metal compound containing 2 displaceable ligand groups with a source of a dianionic ligand, $(L-Z-Y)^{-2}$, optionally, if the precursor compound is in a lower formal oxidation state than the desired product, oxidizing the resulting complex, and optionally, if the precursor compound is in a higher formal oxidation state than the desired product, reducing the resulting complex.

Further according to the present invention there is provided a catalyst system useful for polymerization of addition polymerizable monomers comprising:

A) 1) one or more of the above metal complexes or the reaction product of the above described process, and 2) one or more activating cocatalysts; or B) the reaction product formed by converting one or more of the above metal complexes or the reaction product of the above described process to an active catalyst by use of an activating technique.

The present invention also provides a polymerization process comprising contacting one or more addition polymerizable monomers with a catalyst comprising one or more of the above catalyst systems. The polymerization may be performed under solution, suspension, slurry, or gas phase process conditions, and the composition or individual components thereof may be used in a heterogeneous, i.e., a supported state, or in a homogeneous state. The catalyst can be used in combination with one or more additional catalysts of the same or different nature either simultaneously in the same or separate reactor or sequentially in the same or separate reactors.

Catalysts prepared from the complexes of the present invention possess improved catalytic properties compared to previously known dienyl based metal complexes. Surprisingly, the present complexes are stable under a wide variety of operating conditions and catalyst systems formed therefrom possess desirable operating features. For example, olefin polymer products is formed from catalyst systems comprising complexes according to the present invention are relatively low in undesirable internal vinyl unsaturation thereby making such polymers more resistant to degradation.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Preferably, M is titanium or zirconium, most preferably titanium.

By the term "non-aromatic" when used with reference to L groups is meant that the atoms contributing electrons to the n-system through which the anionic ligand is n-bonded to the metal do not form a cyclic, planar, n-system with 4n+2 electrons, where n is an integer greater than or equal to 0. Examples of suitable L groups include divalent derivatives of pentadienyl-, cyclohexadienyl-, cyclosilahexadienyl-, cycloheptadienyl-, or cyclooctadienyl-groups, or inertly substituted derivatives thereof, as well as the methyldiphenyl group, i.e.:

Examples of aromatic ligand groups which are not included within the present definition of L include cyclopentadienyl ligands and substituted cyclopentadienyl ligands (including indenyl, fluorenyl, and hydrogenated derivatives thereof).

By the term "divalent derivatives" is meant that L is bonded to both Z and M. Suitable inert substituents on L include hydrogen, hydrocarbyl, halocarbyl, halohydrocarbyl, silyl, germyl, halo, amino, phosphino, cyano, hydrocarbyloxy, siloxy and combinations thereof, each of said inert substituents having up to 20 nonhydrogen atoms, or optionally, two or more such substituents (except hydrogen, cyano or halo) together form a ring structure, particularly a fused ring structure. Desirably, such L groups contain up to 50 non-hydrogen atoms. Cyclohexadienyl, dihydronaphthalenyl, hexahydronaphthalenyl, dihydroanthracenyl, hexahydroanthracenyl, decahydroanthracenyl groups and the foregoing inertly substituted derivatives thereof are specifically included within the above definition of L groups.

Preferred L groups correspond to the following formulas:

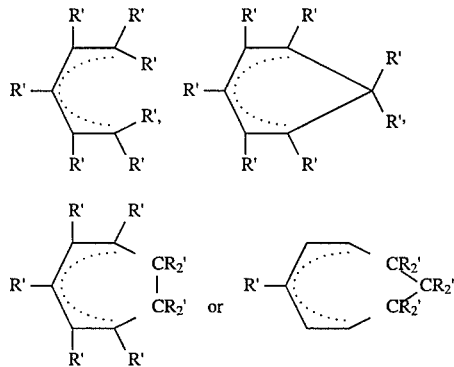

wherein:

R' in each occurrence is a ligand that is independently selected from the group consisting of hydrogen, hydrocarbyl, silyl, germyl, siloxy, amino, hydrocarbyloxy, cyano, halo and combinations thereof, said R' having up to 20 non-hydrogen atoms, and optionally, two or more R' groups (where R' is not hydrogen, halo or cyano) may together form a divalent derivative of one of the foregoing ligands; and provided further that one R' comprises a covalent bond to Z.

Especially suitable L groups are selected from the group consisting of divalent derivatives (as above defined with respect to L) of pentadienyl, cyclohexadienyl, cyclosilahexadienyl, cycloheptadienyl, or cyclooctadienyl groups; hydrocarbyl, silyl, hydrocarbyloxy and siloxy substituted derivatives of such groups; partially hydrogenated anthracenyl, or partially hydrogenated naphthalenyl groups; and hydrocarbyl, silyl, hydrocarbyloxy or siloxy substituted derivatives of such partially hydrogenated anthracenyl or partially hydrogenated naphthalenyl groups.

The dienyl ligand group is bound to the metal atom by any suitable electronic interaction. In certain circumstances the exact form of electronic interaction may be indeterminate, because several equivalent isomeric configurations of the L ligand group may be generated, i.e., $\eta^{1-}$, $\eta^{3-}$, and $\eta^{5-}$ bonded L ligands. This fact has been previously disclosed in the art, particularly in the teachings of R. D. Ernst, *Chem. Rev.*, 88, 1255–1291 (1988), and R. D. Ernst, et al., *J. Am. Chem. Soc.* 107, 5016–5018 (1985). Moreover it is further well understood that the dienyl ligand in an $\eta^5$-bonded configuration may be depicted in several equivalent isomeric configurations, known as the "W", "U" and "S" configurations. Such isomeric forms are illustrated with the 2,4-dimethylpentadien-3-yl ligand in the following drawing:

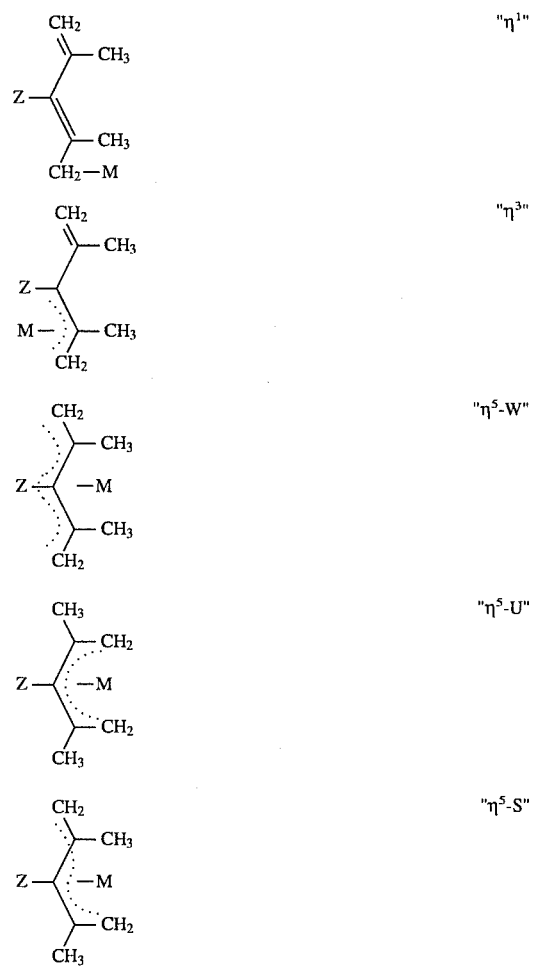

Such variants are not necessarily separately named herein nor are the carbon atoms contributing to the dienyl ligand's bonds always identified since the equivalence of such L groups is well recognized by the skilled artisan, as illustrated by the above cited Ernst and Ernst, et al. references. It is to be further understood that in naming the foregoing L groups, the original positions of the double bonds of the dienyl ligand need not be identified since in the final delocalized ligand group the original double bonds no longer exist, i.e., the $\eta^5$-1,3-pentadien-3-yl group is identical to the $\eta^5$-1,4-pentadien-3-yl group. All such isomers are equivalent and may be referred to simply as $\eta^5$-pentadien-3-yl. For purposes of the present invention it is to be understood that all possible isomeric forms of L are included in any reference to a specific isomer or electronic structure.

The positional numbering of the L group herein is accomplished by identifying the carbons contributing to the bonds to M and Z or where no ambiguity is possible, merely identifying the total carbons contributing to such bonds with the symbol, η. In monocyclic systems the lowest ordinals in sequence are assigned to the carbons contributing to the bonds with the positions otherwise numbered so as to produce the lowest positional numbers for substituted carbon atoms. Thus, the trimethyl-substituted cyclohexadienyl ligand group derived from 1,5,5-trimethyl-1,3-cyclohexadiene and bound at what was the the 2-position (illustrated as follows)

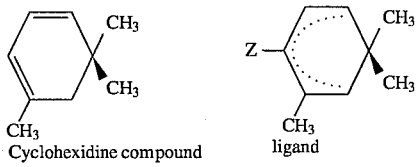

Cyclohexidine compound    ligand is named (2,6,6-trimethyl-η⁵-cyclohexadien-3-yl) rather than (4,6,6-trimethyl-η⁵-cyclohexadien- 3-yl) or (2,2,4-trimethyl-η⁵-cyclohexadien-5-yl). The positional attachment of the Z group is indicated by identifying the carbon atom followed by -yl, i.e., (η⁵-pentadien-1-yl) or (η⁵-pentadien-2-yl). Multicyclic systems are numbered using standard nomenclature so as to avoid confusion. Specifically, hydrogenated naphthalenyl and hydrogenated anthracenyl systems are specifically illustrated as follows:

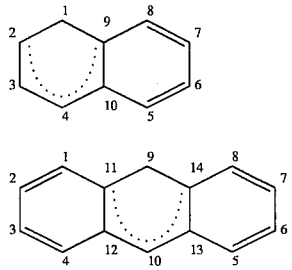

Hydrogenated positions of multicyclic systems are generally identified herein, however it is to be further understood that while various isomeric forms of such hydrogenated ligands are possible they are not necessarily named herein.

Examples of the foregoing L groups include: (η⁵-pentadien-1-yl), (η⁵-pentadien-2-yl), (η⁵-pentadien-3-yl), (2,4-dimethyl-η⁵-pentadien-1-yl), (1, 5-dimethyl-η⁵-pentadien-2-yl), (2, 4-dimethyl-η⁵-pentadien-3-yl), (1, 5-dimethyl-η⁵-pentadien-3-yl), (1, 5-bis(trimethylsilyl)-η⁵-pentadien-3-yl), (η⁵-cyclohexadien-1-yl), (η⁵-cyclohexadien-2-yl), (η⁵-cyclohexadien-3-yl), (6, 6-dimethyl-η⁵-cyclohexadien-1-yl), (6, 6-dimethyl-η⁵-cyclohexadien-2-yl), (6, 6-dimethyl-η⁵-cyclohexadien-3-yl), (6,6-dimethyl-η⁵-6-sila-cyclohexadien-3-yl), (6-t-butyl- 6-methoxy-η⁵-6-sila-cyclohexadien-3-yl), (6-methyl-6-fluoro-η⁵-6-sila-cyclohexadien- 3-yl), (1, 2, 6, 6-tetramethyl-η⁵-cyclohexadien-4-yl), (1,2,4,6,6-pentamethyl-η⁵-cyclohexadien-3-yl), (1, 2, 4, 6, 6-pentamethyl-η⁵-cyclohexadien-5-yl), (1, 2, 5, 6, 6-pentamethyl-η⁵-cyclohexadien-4-yl), (1, 2, 4, 5, 6, 6-hexamethyl-η⁵-cyclohexadien-3-yl), (1,2, 4, 5-tetramethyl-6, 6-cyclotrimethylene-η⁵-cyclohexadien-3-yl), (2, 3, 4, 9, 10-η-1, 2-dihydronaphthalen-1-yl), (2, 3, 4, 9, 10-η-1, 2-dihydronaphthalen-2-yl), (1, 1-dimethyl-2, 3, 4, 9, 10-η-1,2-dihydronaphthalen-2-yl), (1, 1-dimethyl-2, 3, 4, 9, 10-η-1, 2-dihydronaphthalen- 4-yl), diphenylmethyl, di(1-cyclohexenyl)methyl, the equivalent ligands: (1, 1-dimethyl-2, 3, 4, 9, 10-η-1,2, 5, 6, 7, 8-hexahydronaphthalen-4-yl), (1, 1-dimethyl-2, 3, 4, 9, 10-η-1,4, 5, 6, 7, 8-hexahydronaphthalen-4-yl), and (1, 1-dimethyl-2, 3, 4, 9, 10-η-1,5, 6, 7, 8, 9-hexahydronaphthalen-4-yl), the equivalent ligands (1,1,2,3-tetramethyl-2, 3, 4, 9, 10-η-1,2, 5, 6, 7, 8-hexahydronaphthalen-4-yl), (1,1,2,3-tetramethyl-2, 3, 4, 9, 10-η-1,4, 5, 6, 7, 8-hexahydronaphthalen-4-yl), and (1, 1,2, 3-tetramethyl-2, 3, 4, 9, 10-η-1, 5, 6, 7, 8, 9-hexahydronaphthalen-4-yl), (10, 11, 12, 13, 14-η-9, 10-dihydroanthracen-9-yl), (10, 11, 12, 13, 14-η-9,10-dihydroanthracen-1-yl), (9, 9-dimethyl-10, 11, 12, 13, 14-η-9, 10-dihydroanthracen-10-yl), (10, 11, 12, 13, 14-η-1,2,3,4,9, 10-hexahydroanthracen-9-yl), (10, 11, 12, 13, 14-η-1,2, 3, 4, 9,10-hexahydroanthracen-1-yl), (10, 11, 12, 13, 14-η-1,2, 3, 4, 9, 11-hexahydroanthracen-9-yl), (10, 11, 12, 13, 14-η-1,4, 5, 8, 9, 10-hexahydroanthracen-1-yl), (9, 9-dimethyl-10, 11, 12, 13, 14-η-1,4, 5, 8, 9, 10-hexahydroanthracen-10-yl), (9, 9-dimethyl-10, 11, 12, 13, 14-η-1,4, 5, 8, 9, 10-hexahydroanthracen-2-yl), (8, 8-dimethyl- 5, 6, 7, 13, 14-η-1,4, 5, 8, 9,10-hexahydroanthracen-10-yl), the equivalent ligands: (10, 11, 12, 13, 14-η-1,2, 3, 4, 5, 6, 7, 8, 9,10-decahydroanthracen-9-yl) and (10, 11, 12, 13, 14-η-1,2, 3, 4, 5, 6, 7, 8, 9,11-decahydroanthracen- 9-yl); and the equivalent ligands: (9, 9-dimethyl-10, 11, 12, 13, 14-η-1,2, 3, 4, 5, 6, 7, 8, 9,10-decahydroanthracen-10-yl) and (9, 9-dimethyl-10, 11, 12, 13, 14-η-1,2, 3, 4, 5, 6, 7, 8, 9,11-decahydroanthracen-10-yl)

These groups are further illustrated in the following structures:

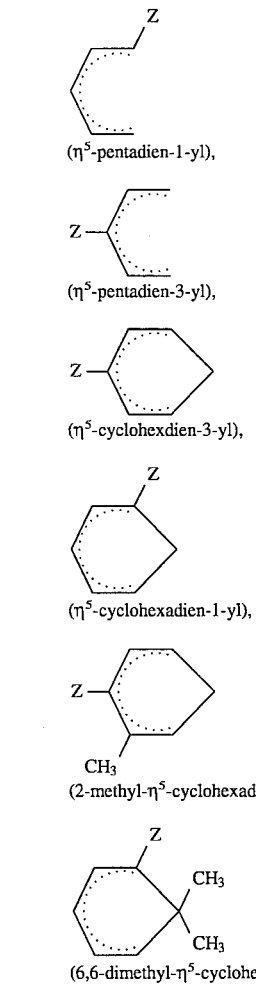

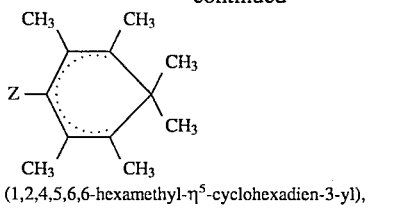
(1,2,4,5,6,6-hexamethyl-η⁵-cyclohexadien-3-yl),

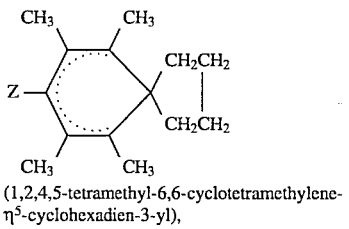
(1,2,4,5-tetramethyl-6,6-cyclotetramethylene-η⁵-cyclohexadien-3-yl),

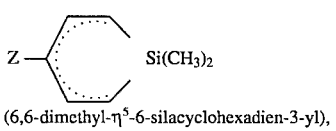
(6,6-dimethyl-η⁵-6-silacyclohexadien-3-yl),

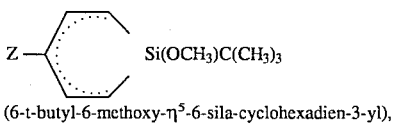
(6-t-butyl-6-methoxy-η⁵-6-sila-cyclohexadien-3-yl),

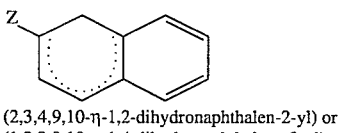
(2,3,4,9,10-η-1,2-dihydronaphthalen-2-yl) or
(1,2,3,9,10-η-1,4-dihydronaphthalene-3-yl),

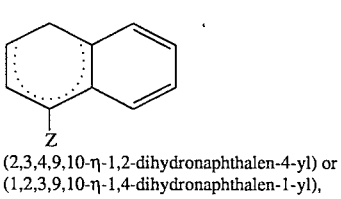
(2,3,4,9,10-η-1,2-dihydronaphthalen-4-yl) or
(1,2,3,9,10-η-1,4-dihydronaphthalen-1-yl),

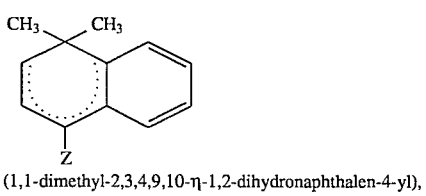
(1,1-dimethyl-2,3,4,9,10-η-1,2-dihydronaphthalen-4-yl),

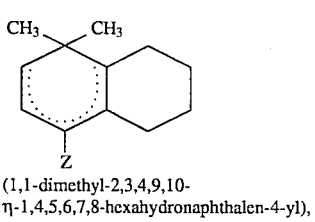
(1,1-dimethyl-2,3,4,9,10-η-1,4,5,6,7,8-hexahydronaphthalen-4-yl),

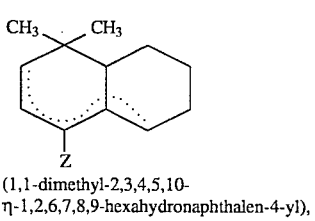
(1,1-dimethyl-2,3,4,5,10-η-1,2,6,7,8,9-hexahydronaphthalen-4-yl),

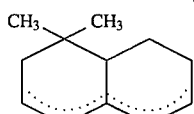
(1,1-dimethyl-3,4,5,6,10-η-1,2,3,7,8,9-hexahydronaphthalen-4-yl),

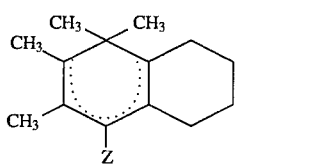
(1,1,2,3-tetramethyl-2,3,4,9,10-η-1,4,5,6,7,8-hexahydronaphthalen-4-yl),

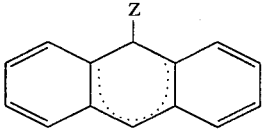
(10,11,12,13,14-η-9,10-dihydroanthracen-9-yl),

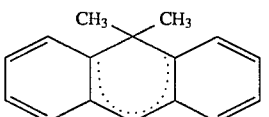
(9,9-dimethyl-10,11,12,13,14-η-9,10-dihydroanthracen-10-yl),

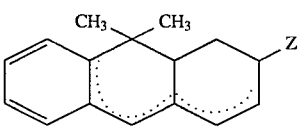
(9,9-dimethyl-4,10,12,13,14-η-1,2,3,4,9,10-hexahydroanthracen-2-yl) or
(9,9-dimethyl-4,10,12,13,14-η-1,2,3,4,9,11-hexahydroanthracen-2-yl),

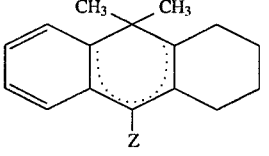
(9,9-dimethy-10,11,12,13,14-η-1,2,3,4,9,10-hexahydroanthracen-10-yl) or
(9,9-dimethyl-10,11,12,13,14-η-1,2,3,4,9,11-hexahydroanthracen-10-yl),

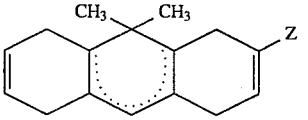
(9,9-dimethyl-10,11,12,13,14-η1,4,5,8,9,10-hexahydroanthracen-10-yl) or
(9,9-dimethyl-10,11,12,13,14-η-1,4,5,8,9,11-hexahydroanthracen-2-yl),

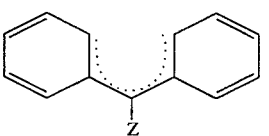
diphenylmethyl,

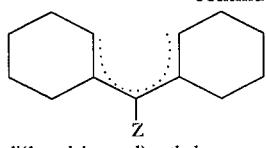

di(1-cyclohexenyl)methyl,

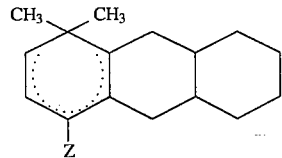

(1,1-dimethyl-2,3,4,11,12-
η-1,4,5,6,7,8,9,10,13,14-decahydroanthracen-4-yl) or
(1,1-dimethyl-2,3,4,11,12-
η-1,5,6,7,8,9,10,11,13,14-decahydroanthracen-4-yl),

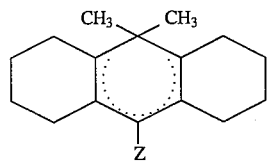

(9,9-dimethyl-10,11,12,13,14-
η-1,2,3,4,5,6,7,8,9,10-decahydroanthracen-10-yl) or
(9,9-dimethyl-10,11,12,13,14-
η1,2,3,4,5,6,7,8,9,11-decahydroanthracen-10-yl)

Preferred examples of X groups include: hydrocarbyl, carboxylate, sulfonate, hydrocarbyloxy, siloxy, amido, phosphido, sulfido, and silyl groups; as well as halo-, amino-, hydrocarbyloxy-, siloxy-, silyl-, and phosphino-substituted derivatives of such hydrocarbyl, carboxylate, sulfonate, hydrocarbyloxy, siloxy, amido, phosphido, sulfido, or silyl groups; hydride, halide and cyanide, said X group having up to 20 nonhydrogen atoms; or alternatively, two X groups together are a hydrocarbadiyl group, preferably a 2-butene-1,4-diyl group, or a substituted 2-butene-1,4-diyl group wherein the substituent is independently each occurrence a hydrocarbyl or silyl group of up to 20 nonhydrogen atoms, said group forming a metallacycle, preferably a metallacyclopentene with M; or, further alternatively, two X groups together form a neutral, 1,4-disubstituted 1,3-butadiene (M being in the +2 formal oxidation state) wherein the substituent is independently each occurrence a hydrocarbyl or silyl group of up to 20 nonhydrogen atoms.

More preferred X groups are hydride, hydrocarbyl (including cyclohydrocarbyl), hydrocarbyloxy, amido (including pyridenyl), silyl, silylhydrocarbyl, siloxy, halide and aminobenzyl. Especially suited are hydride, chloride, methyl, neopentyl, benzyl, phenyl, methoxy, phenoxy, isopropoxy, butoxy, dimethylamido, 2-(N,N-dimethylamino)benzyl, allyl, methylsubstituted allyl (all isomers), pentadienyl, 2-methylpentadienyl, 3methylpentadienyl, 2,4-dimethylpentadienyl, 6,6-dimethylcyclohexadienyl, trimethylsiloxy, and trimethylsilylmethyl.

Preferred X' groups include phosphines, phosphites, ethers, amines, carbon monoxide, salts of Group 1 or 2 metals, and mixtures of the foregoing X' groups. Examples of the foregoing especially include trimethylphosphine, triethylphosphine, trifluorophosphine, triphenylphosphine, bis-1,2-(dimethylphosphino)ethane, trimethylphosphite, triethylphosphite, dimethylphenylphosphite, tetrahydrofuran, diethyl ether, carbon monoxide, pyridine, bipyridine, tetramethylethylenediamine (TMEDA), dimethoxyethane (DME), dioxane, triethylamine, lithium chloride, and magnesium chloride.

Further preferred metal coordination complexes according to the present invention correspond to the formula:

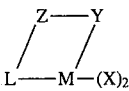

wherein:

Y is —O—, —S—, —NR*—, —PR*—;

Z is SiR*$_2$, CR*$_2$, SiR*$_2$SiR*$_2$, CR*$_2$CR*$_2$, CR*=CR*, CR*$_2$SiR*$_2$, CR*$_2$CR*$_2$CR*$_2$, CR*$_2$SiR*$_2$CR*$_2$, SiR*$_2$CR*$_2$CR*$_2$, SiR*$_2$CR*$_2$SiR*$_2$, SiR*$_2$SiR*$_2$CR*$_2$, SiR*$_2$SiR*$_2$SiR*$_2$, or GeR*$_2$; wherein:

R* each occurrence is independently hydrogen, or a member selected from hydrocarbyl, silyl, halogenated alkyl, halogenated aryl, and combinations thereof, said R* having up to 18 non-hydrogen atoms, and optionally (when R* is not hydrogen), two R* groups from Z, or an R* group from Z and an R* group from Y form a ring system.

M is titanium or zirconium in the +2 or +4 formal oxidation state;

L is a divalent derivative of a pentadienyl, cyclohexadienyl, cyclosilahexadienyl, partially hydrogenated naphthalenyl, partially hydrogenated anthracenyl group or a hydrocarbyl or silyl substituted derivative of such cyclohexadienyl, cyclosilahexadienyl, partially hydrogenated naphthalenyl, partially hydrogenated anthracenyl group, each said hydrocarbyl or silyl substituent having up to 10 nonhydrogen atoms; and X is chloro, hydrocarbyl, hydrocarbyloxy or an N, N-dialkylamino substituted hydrocarbyl group, said X having up to 12 non-hydrogen atoms.

Most highly preferred metal coordination complexes are amidosilane- or amidoalkanediyl- compounds corresponding to the formula:

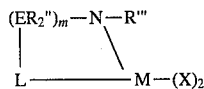

wherein:

E is independently each occurrence silicon or carbon.

R" is independently each occurrence hydrogen or C$_{1-10}$ hydrocarbyl;

R'" is an aryl, benzyl, hydrocarbyl substituted aryl, hydrocarbyl substituted benzyl, secondary or tertiary alkyl or tertiary silyl group of up to 12 nonhydrogen atoms;

M is titanium in the +4 formal oxidation state;

m is an integer from 1 to 3;

L is a (2,4-disubstituted pentadien-3-yl), (2,4-disubstituted pentadien-1-yl), (1,5-disubstituted pentadien-3-yl), (6,6-disubstituted-η$^5$-cyclohexadien-3-yl), (6,6-disubstituted-η$^5$-cyclosilahexadien-3-yl), (1,2, 3, 4, 5-η$^5$-cyclohexadien-6-yl), (6-substituted-1, 2, 3, 4, 5-η-cyclohexadien-6-yl), (1,2, 4, 5, 6, 6-hexasubstituted-η$^5$-cyclohexadien-3-yl)-, (1, 1-disubstituted-η$^5$-hexahydronaphthalen-4-yl), (1, 1, 2, 3-tetrasubstituted-η$^5$-hexahydronaphthalen-4-yl), or (9, 9-disubstituted-10, 11, 12, 13, 14-η-1,2, 3, 4, 5, 6, 7, 8, 9, 10-decahydroanthracene-10-yl), said substituents independently each occurrence being hydrocarbyl, hydrocarbyloxy, silyl, siloxy or a mixture thereof of up to 10 nonhydrogen atoms each; and X is methyl, allyl, phenyl, benzyl, chloro,2-(N,N-dimethylamino)benzyl or trimethylsilylmethyl.

As a means of further illustration of the invention, specific metal complexes included therein are:

Pentadienyl and substituted pentadienyl complexes (N-tert-butylamido)(dimethyl)(2,4-dimethyl-$\eta^5$-pentadien-1-yl)silanetitanium(IV) dichloride; (N-tert-butylamido)(dimethyl)(2,4-dimethyl-$\eta^5$-pentadien-3-yl)silanetitanium (IV) dimethyl; (N-tert-butylamido)(diphenyl)( 2,4-dimethyl-$\eta^5$-pentadien-3-yl)silanetitanium (IV) dimethyl; (N-benzylamido)(dimethyl)(2,4-dimethyl-$\eta^5$-pentadien-3-yl)silanetitanium (IV) dimethyl; (N-tert-butylamido)(tetramethyl)(2,4-dimethyl-$\eta^5$-pentadien-3-yl)disilanetitanium (IV) dimethyl; (N-tert-butylamido)(tetramethyl) (1,5-bis(trimethylsilyl)-2,4-dimethyl-$\eta^5$-pentadien-1-yl)disilanetitanium (IV) dimethyl; (N-tert-butylamido)(1,1,2,2-tetramethyl)(1,5-bis(trimethylsilyl) 2,4-dimethyl-$\eta^5$-pentadien-3-yl)disilanetitanium (IV) dimethyl; (N-tert-butylamido)( 1,1,2,2-tetramethyl)($\eta^5$-2,4-pentadien-3-yl)disilanetitanium (IV)-dimethyl; (N-tert-butylamidomethylene)(dimethyl)(2,4-dimethyl-$\eta^5$-pentadien-3-yl)silanetitanium (IV) dimethyl; (N-tert-butylamido)(dimethyl)(2,4-dimethyl-$\eta^5$-pentadien-3-ylmethylene)silanetitanium (IV) dimethyl; (N-tert-butylamido)(dimethyl)( 2,4-dimethyl-$\eta^5$-pentadien-3-yl)silanetitanium (IV)-methyl 2-(N,N-dimethylamino)benzyl; (N-tert-butylamido)(dimethyl)(2,4-dimethyl-$\eta^5$-pentadien-1-yl)silanetitanium (IV) methyl ($\eta^3$-propenyl); (N-tert-butylamido)(dimethyl)( 1,5-dimethyl-$\eta^5$-pentadien-3-yl)silanetitanium (IV)-dichloride; (N-tert-butylamido)(dimethyl)(1,5-dimethyl-$\eta^5$-pentadien-3-yl)silanetitanium (II) $\eta^4$-1,4-diphenyl-1,3-butadiene; (N-tert-butylamido)(dimethyl)( 2,4-dimethyl-$\eta^5$-pentadien-3-yl)silanetitanium (II)$\eta^4$-2,3-dimethyl-1,3-butadiene; (N-tert-butylamido)(dimethyl)(2,4-dimethyl-$\eta^5$-pentadien-1-yl)silanetitanium (IV) ($\eta^5$-pentadienyl) chloride; (N-phenyl)(dimethyl)( 2,4-dimethyl-$\eta^5$-pentadien-1-yl)silanetitanium(IV) diphenyl; (N-cyclododecyl)(dimethyl)(2,4-dimethyl-$\eta^5$-pentadien-3-yl)silanetitanium (IV) dibenzyl; (N-tert-butylamido)(dimethyl)(1,5-dimethyl-$\eta^5$-pentadien-3-yl)silanetitanium (IV) bis(trimethylsilylmethyl); (N-tertamylamido)(dimethyl)( 2,4-dimethyl-$\eta^5$-pentadien-1-yl)silanetitanium (IV) dimethoxy; 1-(N-tert-butylamido)-2-(2,4-dimethyl-$\eta^5$-pentadien-3-yl)ethane-1,2-diyltitanium (IV) dimethyl; (N-tert-butylamido)(dimethyl)(1,5-di(trimethylsilyl) 2,4-dimethyl-$\eta^5$-pentadien-3-yl)silanetitanium (IV) dimethyl; and (N-tert-butylamido)(dimethyl)(1,5-bis(trimethylsilyl)-$\eta^5$-pentadien-3-yl)silanetitanium (IV) dimethyl.

Cyclohexadienyl and substituted cyclohexadienyl complexes (N-tert-butylamido)(dimethyl)($\eta^5$-cyclohexadien-1-yl)silanetitanium(IV) dichloride; (N-tert-butylamido)(dimethyl)($\eta^5$-cyclohexadien-1-yl)silanetitanium (IV) dimethyl; (N-tert-butylamido)(dimethyl)(6,6-dimethyl-$\eta^5$-cyclohexadien-1-yl)silanetitanium (IV) dimethyl; (N-tert-butylamido)(dimethyl)(6,6-dimethyl-$\eta^5$-cyclohexadien-3-yl)silanetitanium (IV) dimethyl; (N-tert-butylamido)(diphenyl)( 6,6-dimethyl-$\eta^5$-cyclohexadien-3-yl)silanetitanium (IV) dimethyl; (N-tert-butylamido)(1,1,2,2-tetramethyl)(6,6-dimethyl-$\eta^5$-cyclohexadien-1-yl)disilanetitanium (IV) dimethyl; (N-tert-butylamido)(1,1,2,2-tetramethyl)( 6,6-dimethyl-$\eta^5$-cyclohexadien-3-yl)disilanetitanium (IV) dimethyl; ((N-tert-butylamido)methyl)(dimethyl)(6,6-dimethyl-$\eta^5$-cyclohexadien-3-yl)silanetitanium (IV) dimethyl; (N-tert-butylamido)(dimethyl)(( 6,6-dimethyl-$\eta^5$-cyclohexadien-3-yl)methyl)silanetitanium (IV) dimethyl; (N-tert-butylamido)(dimethyl)(2,4-dimethoxy- 6,6-dimethyl-$\eta^5$-cyclohexadien-3-yl)silanetitanium (IV) dimethyl; (N-benzylamido)(dimethyl)( 6,6-dimethyl-$\eta^5$-cyclohexadien-3-yl)silanetitanium (IV) dimethyl; (N-tert-butylamido)(dimethyl)(1, 2, 4, 5, 6, 6-hexamethyl-$\eta^5$-cyclohexadien-3-yl)silanetitanium (IV) dimethyl; (N-tert-butylamido)(dimethyl)( 1,2,6,6-tetramethyl-$\eta^5$-cyclohexadien-3-yl)silanetitanium (IV) dimethyl; (N-tert-butylamido)(dimethyl)(6, 6-dimethyl-$\eta^5$-cyclohexadien-3-yl)silanetitanium (IV) methyl 2-(N,N-dimethyl)aminobenzyl; (N-tert-butylamido)(dimethyl)($\eta^5$-cyclohexadien-1-yl)silanetitanium (IV) ($\eta^3$-propenyl)bromide; (N-tert-butylamido)(dimethyl)(6, 6-dimethyl-$\eta^5$-cyclohexadien-3-yl)silanetitanium (II) $\eta^4$-1, 4-diphenyl-1,3-butadiene; (N-tert-butylamido)(dimethyl)($\eta^5$-cyclohexadien-1-yl)silanetitanium (II) (1,4-diphenyl-$\eta^4$-1,3-butadiene); (N-tert-butylamido)(dimethyl)(6, 6-dimethyl-$\eta^5$-cyclohexadien-3-yl)silanetitanium (IV) ($\eta^5$-pentadienyl) chloride; (N-phenyl)(dimethyl)( 6, 6-dimethyl-$\eta^5$-cyclohexadien-3-yl)silanetitanium(IV) diphenyl; (N-dodecyl)(dimethyl)(6, 6-dimethyl-$\eta^5$-cyclohexadien-3-yl)silanetitanium (IV) dibenzyl; (N-tert-butylamido)(dimethyl)(6, 6-dimethyl-$\eta^5$-cyclohexadien-3-yl)silanetitanium (IV) bis(trimethylsilylmethyl); (N-tertamylamido)(dimethyl)( 6, 6-dimethyl-$\eta^5$-cyclohexadien-3-yl)silanetitanium(IV) dimethoxy; 1-(N-tert-butylamido)-2-(6, 6-dimethyl-$\eta^5$-cyclohexadien-3-yl)ethanetitanium (IV) dimethyl; (N-tert-butylamido)(dimethyl)(2, 3, 4, 9, 10-$\eta$-1,2-dihydronaphthalen-4-yl)silanetitanium (IV) dimethyl; (N-tert-butylamido)(dimethyl)( 1, 1-dimethyl-2, 3, 4, 9, 10-$\eta$-1,4-dihydronaphthalen-4-yl)silanetitanium (IV) dimethyl; (N-tert-butylamido)(dimethyl)(2, 3, 4, 9, 10-$\eta$- 1,2, 5, 6, 7, 8-hexahydronaphthalen-1-yl)silanetitanium (IV) dimethyl; (N-tert-butylamido)(dimethyl)( 1,1-dimethyl-2, 3, 4, 9, 10-$\eta$-1,2, 5, 6, 7, 8-hexahydronaphthalen-4-yl)silanetitanium (IV) dimethyl; (N-tert-butylamido)(dimethyl)(9, 9-dimethyl-10, 11, 12, 13, 14-$\eta$-9,10-dihydroanthracen-10-yl)silanetitanium (IV) dimethyl; (N-tert-butylamido)(dimethyl)(9,9-dimethyl-10, 11, 12, 13, 14-$\eta$ -1, 2, 3, 4, 9, 10-hexahydroanthracen-10-yl)silanetitanium (IV) dimethyl; (N-tert-butylamido)(dimethyl)( 9, 9-dimethyl-10, 11, 12, 13, 14-$\eta$-1, 2, 3, 4, 5, 6, 7, 8, 9, 10-decahydroanthracen-10-yl)silanetitanium (IV) dimethyl, and (N-tert-butylamido)(dimethyl)( 9, 9-dimethyl-10, 11, 12, 13, 14-$\eta$-1, 2, 3, 4, 5, 6, 7, 8, 9, 11-decahydroanthracen-10-yl)silanetitanium (IV) dimethyl.

Higher cycloalkadienyl and other complexes (N-tert-butylamido)(dimethyl)($\eta^5$-cycloheptadien-1-yl)silanetitanium(IV) dichloride; (N-tert-butylamido)(dimethyl)($\eta^5$-cyclooctadien-1-yl)silanetitanium (IV) dimethyl; (N-tert-butylamido)(dimethyl)($\eta^5$-cyclooctadien-3-yl)silanetitanium (IV) dimethyl; (N-tert-butylamido)(dimethyl)(6, 6, 7, 7-tetramethyl-$\eta^5$-cycloheptadien-3-yl)silanetitanium (IV) dimethyl; (N-tert-butylamido)(dimethyl)( 6, 7, 8-trimethyl-$\eta^5$-cyclooctadien-3-yl)silanetitanium (IV) dimethyl; (N-tert-butylamido)(1, 1, 2, 2-tetramethyl)(6,6-dimethyl-$\eta^5$-cycloheptadien-3-yl)disilanetitanium (IV) dimethyl; (N-tert-butylamido)(1,1,2,2-tetramethyl)( 6, 7, 8-trimethyl-$\eta^5$-cyclooctadien-3-yl)disilanetitanium (IV) dimethyl; (N-tert-butylamido)(dimethyl)($\eta^5$-di(1-cyclohexenyl)methyl)silanetitanium (IV) dimethyl; (N-tert-butylamidomethyl)(dimethyl)($\eta^5$-diphenylmethyl)silanetitanium (IV) dimethyl; (N-tert-butylamido)(dimethyl)($\eta^5$-diphenylmethyl)silanetitanium (IV) dichloro; (N-tert-butylamido)(dimethyl)($\eta^5$-diphenylmethyl)silanetitanium (IV) dimethyl; (N-tert-butylamido)(dimethyl)( 6, 6-dimethyl-$\eta^5$-cyclosilahexadien-3-yl)silanetitanium (IV) dimethyl; (N-tertbutylamido)(dimethyl)(6-t-butyl-6-methoxy-$\eta^5$-cyclosilahexadien-3-yl)silanetitanium (IV) dimethyl; (N-tert-butylamido)(dimethyl)( 6-methyl-6-methoxy-$\eta^5$-cyclosilahexadien-3-yl)silanetitanium (IV) dimethyl; and (N-tert-butylamido)(dimethyl)(6, 7, 7, 8-tetramethyl-$\eta^5$-cyclooctadien-3-yl)silanetitanium (II) $\eta^4$-1,4-diphenyl-1,3-butadiene.

The skilled artisan will recognize that additional members of the foregoing list will include the corresponding zirconium or hafnium containing derivatives, as well as complexes that are variously substituted as herein defined.

Most highly preferred metal complexes according to the present invention comprise: (tert-butylamido)(dimethyl)($\eta^5$-pentadien-3-yl)silanetitanium dichloride; (tert-butylamido)(dimethyl)($\eta^5$-pentadien-3-yl)silanetitanium dimethyl; (tert-butylamido)(dimethyl)(2,4-dimethyl-$\eta^5$-pentadien-3-yl)silanetitanium dichloride; (tert-butylamido)(dimethyl)(2, 4-dimethyl-$\eta^5$-pentadien-3-yl)silanetitanium dimethyl; (tert-butylamido)(dimethyl)($\eta^5$--pentadien-3-yl)silanezirconium dichloride; (tert-butylamido)(dimethyl)($\eta^5$-pentadien-1-yl)silanezirconium dimethyl; (tert-butylamido)(dimethyl)( 2,4-dimethyl-$\eta^5$-pentadien-3-yl)silanezirconium dichloride; (tert-butylamido)(dimethyl)(2,4-dimethyl-$\eta^5$-pentadien-3-yl)silanezirconium dimethyl; (tert-butylamido)(dimethyl)(1, 5-bis(trimethylsilyl)-2,4-dimethyl-$\eta^5$-pentadien-3-yl)silanetitanium dichloride; (tert-butylamido)(dimethyl)(1,5-bis(trimethylsilyl)-2,4-dimethyl-$\eta^5$-pentadien-3-yl)silanetitanium dimethyl; (tert-butylamido)(dimethyl)(1, 5-bis(trimethylsilyl)-2,4-dimethyl-$\eta^5$-pentadien-3-yl)silanezirconium dichloride; (tert-butylamido)(dimethyl)(1,5-bis(trimethylsilyl)-2,4-dimethyl-$\eta^5$-pentadien-3-yl)silanezirconium dimethyl; (tert-butylamido)(dimethyl)(6,6-dimethyl-$\eta^5$-cyclohexadien-3-yl)silanetitanium dichloride; (tert-butylamido)(dimethyl)(6, 6-dimethyl-$\eta^5$-cyclohexadien-3-yl)silanetitanium dimethyl; (tert-butylamido)(dimethyl)(6,6-dimethyl-$\eta^5$-cyclosilahexadien-3-yl)silanetitanium dichloride; (tert-butylamido)(dimethyl)( 6,6-dimethyl-$\eta^5$-cyclosilahexadien-3-yl)silanetitanium dimethyl; (tert-butylamido)(dimethyl)(6,6-dimethyl-$\eta^5$-cyclohexadien-3-yl)silanezirconium dichloride; (tert-butylamido)(dimethyl)(6,6-dimethyl-$\eta^5$-cyclohexadien-3-yl)silanezirconium dimethyl, (tert-butylamido)(dimethyl)(6,6-dimethyl-$\eta^5$-cyclosilahexadien-3-yl)silanezirconium dichloride; (tert-butylamido)(dimethyl)( 6,6-dimethyl-$\eta^5$-cyclosilahexadien-3-yl)silanezirconium dimethyl, (N-tert-butylamido)(dimethyl)(2, 3, 4, 9, 10-$\eta$-1, 2-dihydronaphthalen-4-yl)silanetitanium (IV) dimethyl; (N-tert-butylamido)(dimethyl)( 1, 1-dimethyl-2, 3, 4, 9, 10-$\eta$-1,4-dihydronaphthalen-4-yl)silanetitanium (IV) dimethyl; (N-tert-butylamido)(dimethyl)(2, 3, 4, 9, 10-$\eta$- 1,2, 5, 6, 7, 8-hexahydronaphthalen-4-yl)silanetitanium (IV) dimethyl; (N-tert-butylamido)(dimethyl)( 1,1-dimethyl-2, 3, 4, 9, 10-$\eta$-1,2, 5, 6, 7, 8-hexahydronaphthalen-4-yl)silanetitanium (IV) dimethyl; (N-tert-butylamido)(dimethyl)(9, 9-dimethyl-10, 11, 12, 13, 14-$\eta$-9,10-dihydroanthracen-10-yl)silanetitanium (IV) dimethyl; (N-tert-butylamido)(dimethyl)(9,9-dimethyl-10, 11, 12, 13, 14-$\eta$-1,2, 3, 4, 9, 10-hexahydroanthracen-10-yl)silanetitanium (IV) dimethyl; (N-tert-butylamido)(dimethyl)( 9, 9-dimethyl-10, 11, 12, 13, 14-$\eta$-1,2, 3, 4, 5, 6, 7, 8, 9, 10-decahydroanthracen-10-yl)silanetitanium (IV) dimethyl, and (N-tert-butylamido)(dimethyl)( 9, 9-dimethyl-10, 11, 12, 13, 14-$\eta$-1,2, 3, 4, 5, 6, 7, 8, 9, 11-decahydroanthracen-10-yl)silanetitanium (IV) dimethyl.

The complexes can be prepared in one embodiment by combining a precursor metal compound corresponding to the formula $M(X)_4X'_q$, wherein M, X, X' and q are as previously defined, with the added proviso that X in two occurrences is a monovalent anionic moiety having up to 20 non-hydrogen atoms capable of displacement by a dianion ligand, $(L-Z-Y)^{-2}$, wherein L, Z, and Y are as previously defined, with a metallated derivative of the dianion ligand $(Z-L-Y)^{-2}$, with a silyl-, especially a trialkylsilyl-, derivative of the dianion ligand $(Z-L-Y)^{-2}$, said silyl- or trialkylsilyl-group having from 1 to 20 nonhydrogen atoms, or with the neutral compound, H-(Z-L-Y)-H. The reaction may optionally be performed in the presence of a reducing agent or in the presence of a Lewis base, X'. The reaction is preferably conducted in an inert, organic, liquid at a temperature from −100° to 300° C., preferably from −78° to 150° C., most preferably from 0° to 125° C. and optionally recovering the complex. Suitable metallated derivatives especially include lithium, sodium, potassium, magnesium, or Grignard derivatives of the dianion ligand. Suitable trialkylsilyl derivatives especially include trimethylsilyl derivatives of the dianion ligand. Suitable reducing agents especially include n-butyl lithium, lithium or magnesium.

In a preferred embodiment, the complexes wherein M is in the +4 formal oxidation state can be prepared by contacting a precursor metal compound wherein the metal is in the +3 formal oxidation state, corresponding to the formula: $M(X)_3X'_q$, wherein M, X, X' and q are as previously defined, with the proviso that X in two occurrences is a monovalent anionic moiety having up to 20 non-hydrogen atoms capable of displacement by a dianion ligand, $(L-Z-Y)^{-2}$, wherein L, Z, and Y are as previously defined, with the above sources of the dianionic ligand, $(L-Z-Y)^{-2}$; and thereafter oxidizing the metal center with an organic halogen containing oxidizing agent, or a metal halide oxidizing agent. Particularly preferred oxidizing agents are methyl chloride, methylene chloride, chloroform, carbon tetrachloride, $PbCl_2$ and AgCl.

The dianionic ligand group is prepared using standard synthetic measures known to the skilled artisan or by use of procedures analogous to known routes. The ligands containing cyclosilahexadienyl functionality are prepared in a manner analogous to the techniques disclosed in Jutzi, et al, *Chem. Ber.*, 117, 1885–95 (1984); *J. Am. Chem. Soc.*, 103 6788–6789 (1981); and *Zh. Oshch. Khim.*, 44, 226–227 (1979), modified according to EP-A-563,365 as to the particular silane ligand utilized.

Suitable reaction media for the formation of the complexes are aliphatic and aromatic hydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and styrene, alkyl ethers having from 1 to 4 carbons in each alkyl group; $C_{1-4}$ dialkyl ether derivatives of (poly)alkylene glycols, and tetrahydrofuran. Mixtures of the foregoing are also suitable. Preferred solvents include $C_{5-10}$ alkanes, dialkyl ethers having from 1 to 4 carbons in each alkyl group, tetrahydrofuran, toluene, and mixtures thereof. Solvated adducts of the metal precursor complex may also be used if desired. Examples of solvated adducts include pyridine-, diethylether-, tetrahydrofuran- (THF), 1,2-dimethoxyethane- (DME), or tetramethyl-ethylenediamine- (TMEDA) containing adducts.

The complexes according to the present invention are surprisingly stable and readily synthesized. They are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), WO 93-23412 (equivalent to U.S. Ser. No. 07/876,268), and EP-A- 520,732 (equivalent to U.S. Ser. Nos. 07/884,966 filed May 1, 1992 now U.S. Pat. No. 5,350,723), the teachings of which are hereby incorporated by reference.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts.

Suitable ion forming compounds useful as cocatalysts in one embodiment of the present invention comprise a cation which is a Bronsted acid capable of donating a proton, and a compatible, noncoordinating anion, A-. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

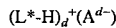

wherein:
L* is a neutral Lewis base;
(L*-H)+ is a Bronsted acid;
$A^{d-}$ is a noncoordinating, compatible anion having a charge of d–, and
d is an integer from 1 to 3.

More preferably $A^{d-}$ corresponds to the formula: $[M'^{k+}Q_{n'}]^{d-}$
wherein:
k is an integer from 1 to 3;
n' is an integer from 2 to 6;
n'-k=d;
M' is an element selected from Group 13 of the Periodic Table of the Elements; and
Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, i.e., the counter ion has a single negative charge and is A–. Activating cocatalysts comprising boron which are particularly useful in the preparation of catalysts of this invention may be represented by the following general formula: $[L^*-H]^+ [BQ_4]^-$
wherein:
L* is as previously defined;
B is boron in a valence state of 3; and
Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetraphenylborate, triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetratphenylborate,
N,N-diethylanilinium tetraphenylborate,
N,N-dimethyl-2,4,6-trimethylanilinium tetraphenylborate,
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate, N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldiimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl) borate,
N,N-diethylanilinium tetrakis(pentafluorophenyl) borate,
N,N-dimethyl-2,4,6-trimethylanilinium tetrakis(pentafluorophenyl) borate,
trimethylammonium tetrakis(2,3,4,6-tetrafluorophenyl)borate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl) borate,
N,N-dimethylanilinium tetrakis(2,3,4,6-tetrafluorophenyl) borate,
N,N-diethylanilinium tetrakis(2,3,4,6-tetrafluorophenyl) borate, and
N,N-dimethyl-2,4,6-trimethylanilinium tetrakis(2,3,4,6-tetrafluorophenyl) borate;
dialkyl ammonium salts such as:
di-(i-propyl)ammonium tetrakis(pentafluorophenyl) borate, and
dicyclohexylammonium tetrakis(pentafluorophenyl) borate;
tri-substituted phosphonium salts such as:
triphenylphosphonium tetrakis(pentafluorophenyl) borate,
tri(o-tolyl)phosphonium tetrakis(pentafluorophenyl) borate, and
tri(2,6-dimethylphenyl)phosphonium tetrakis(pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(2,6-dimethylphenyl)oxonium tetrakis(pentafluorophenyl) borate;
di-substituted sulfonium salts such as:
diphenylsulfonium tetrakis(pentafluorophenyl) borate,
di(o-tolyl)sulfonium tetrakis(pentafluorophenyl) borate, and
di(2,6-dimethylphenyl)sulfonium tetrakis(pentafluorophenyl) borate.

Preferred [L*-H]+cations are N,N-dimethylanilinium and tributylammonium.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$©^+ A^-$$

wherein:

$©^+$ is a $C_{1-20}$ carbenium ion; and
A− is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R_3Si(X')_q{}^+A^-$$

wherein:

R is $C_{1-10}$ hydrocarbyl, and X', q and A− are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm:*, 1993, 383–384, as well as Lambert, J. B., et al., *Organometallics*, 1994, 13, 2430–2443. The use of the above silylium salts as activating cocatalysts for addition polymerization catalysts is claimed in United States Patent Application entitled, Silylium Cationic Polymerization Activators For Metallocene Complexes, filed in the names of David Neithamer, David Devore, Robert LaPointe and Robert Mussell on even date herewith U.S. Ser. No. 304,314.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0° to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula $G+A-$; wherein:

G+ is a cation which is nonreactive towards the starting and resulting complex, and A– is as previously defined.

Examples of cations, G+, include tetrahydrocarbyl substituted ammonium or phosphonium cations having up to 40 nonhydrogen atoms. Preferred cations are the tetra-n-butylammonium- and tetraethylammoniumcations.

During activation of the complexes of the present invention by bulk electrolysis the cation of the supporting electrolyte passes to the counter electrode and A– migrates to the working electrode to become the an ion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra-n-butylammonium tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned United States Patent application entitled, "Silylium Cationic Polymerization Activators For Metallocene Complexes", filed on even date herewith.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:10 to 1:1. In a particularly preferred embodiment of the invention the cocatalyst can be used in combination with a tri(hydrocarbyl)aluminum compound having from 1 to 10 carbons in each hydrocarbyl group or an oligomeric or polymeric alumoxane. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 2 to 6 carbons in each alkyl group, especially those wherein the alkyl groups are methyl, ethyl, propyl, isopropyl, n-butyl, isobutyl, pentyl, neopentyl, or isopentyl, and methylalumoxane, modified methylalumoxane (that is, methylalumoxane modified by reaction with triisobutyl aluminum) (MMAO) and isobutylalumoxane. The molar ratio of metal complex to aluminum compound is preferably from 1:10,000 to 100:1, more preferably from 1:1000 to 10:1, most preferably from 1:500 to 1:1. A most preferred activating cocatalyst comprises both a strong Lewis acid and an alumoxane, especially tris(pentafluorophenyl)borane and methylalumoxane, modified methylalumoxane, or diisobutylalumoxane.

Upon activation of the metal complexes containing two distinct X groups, utilizing one of the preceding cation forming activating cocatalysts or activating techniques, there is believed to be formed, without wishing to be bound by such belief, a cationic metal complex corresponding to the formula:

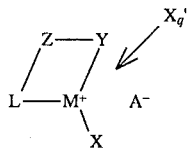

wherein:

M is a Group 4 metal in the +4 formal oxidation state, and L, Z, Y, X', X, and q are as previously defined, and A– is as previously defined and is the noncoordinating anion from the activating cocatalyst or is formed concurrently by the activating technique.

Utilizing the preferred neutral Lewis acid activating cocatalyst, $B(C_6F_5)_3$, A– of the foregoing cationic metal complexes is believed to correspond to the formula: $XB(C_6F_5)_3-$, wherein X is a $C_{1-10}$ hydrocarbyl group. Most preferably A– is $B(C_6F_5)_4^-$ or $XB(C_6F_5)_3^-$, wherein X is a $C_{1-10}$ hydrocarbyl group.

It is further believed, without wishing to be bound by such belief, that Group 4 metal complexes in the +4 oxidation state wherein two X groups together with the metal M form a metallacycle, uniquely form novel zwitterionic complexes upon activation by combination with the previously mentioned neutral Lewis acid activating cocatalysts. Such zwitterionic metal complexes are believed correspond to the formula:

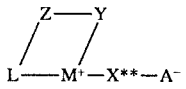

wherein:

M is a Group 4 metal in the +4 oxidation state;

L, Z, Y, are as previously defined;

X** is the divalent remnant formed by ring opening at one of the carbon to metal bonds of the metallacycle formed by M and two X groups taken together; and A– is the moiety derived from a neutral Lewis acid activating cocatalyst.

Such zwitterionic complexes preferably correspond to one of the two equilibrium structures of the formula:

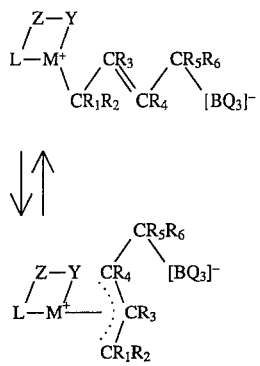

wherein:

M is titanium or zirconium;

L, Z, and Y are as previously defined;

$R_1$, $R_2$, $R_3$, $R_4$, $R_5$, and $R_6$ are independently each occurrence hydrogen or a hydrocarbyl or silyl group having from 1 to 20 nonhydrogen atoms;

B is boron in a valence state of 3, and

Q is as previously defined.

The catalysts may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain, macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1, 5-hexadiene, 1,7-octadiene, vinylcyclohexane, 4-vinylcyclohexene, allylbenzene, divinylbenzene, 2,5-norbornadiene and mixtures of such other preferred monomers with $C_{2-20}$ α-olefins.

In general, the polymerization may be accomplished at conditions well known in the prior art for Ziegler-Natta or Kaminsky-Sinn type polymerization reactions, i.e., temperatures from 0°–250° C. and pressures from atmospheric to 10,000 atmospheres (0.1 to 1000 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase or slurry polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents or diluents for polymerization are non-coordinating, inert liquids. Examples include $C_{4-10}$ straight and branched-chain hydrocarbons, especially butane, isobutane, pentane, isopentane, hexane, heptane, octane, and mixtures thereof; cyclic and alicyclic hydrocarbons such as cyclopentane, cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene (all isomers). Suitable solvents also include liquid olefins or other monomers or mixtures thereof as previously mentioned.

The catalysts may also be utilized in combination with at least one additional homogeneous or heterogeneous polymerization catalyst in the same or separate reactors connected in series or in parallel to prepare polymer blends having desirable properties. An example of such a process is disclosed in WO 94/00500, equivalent to U.S. Ser. No. 07/904,770, now abn as well as U.S. Ser. No. 08/10958, filed Jan. 29, 1993, now abandoned the teachings of which are hereby incorporated by reference herein.

One such polymerization process comprises:

contacting, optionally in a solvent, one or more α-olefins with a catalyst according to the present invention comprising one or more metal complexes according to the present invention in one or more continuous stirred tank or tubular reactors, or in the absence of solvent, optionally in one or more fluidized bed gas phase reactors, connected in series or in parallel, and recovering the resulting polymer.

In another such polymerization process, in one or more of the foregoing reactors, one or more α-olefins are also contacted with one or more catalyst compositions comprising one or more metal complexes according to the present invention in admixture with a catalyst composition comprising one or more homogeneous metallocene complexes other than a complex according to the present invention, said catalyst composition also comprising one or more cocatalyst activators.

In yet another process an ethylene/α-olefin interpolymer composition is prepared by:

(A) contacting ethylene and at least one other α-olefin under polymerization conditions in the presence of a homogeneous catalyst composition of the present invention comprising a metal complex of the present invention with at least one of the aforementioned activating cocatalysts in at least one reactor to produce a first interpolymer or optionally a solution of a first interpolymer, (B) contacting ethylene and at least one other α-olefin under polymerization conditions at optionally a different, preferably a higher, polymerization reaction temperature than used in step (A) in the presence of a heterogeneous Ziegler catalyst in at least one other reactor to produce a second interpolymer optionally in solution, and (C) combining the first interpolymer and second interpolymer to form an ethylene/α-olefin interpolymer blend composition, and (D) recovering the ethylene/α-olefin interpolymer blend composition.

Preferably the heterogeneous Ziegler catalyst comprises:

(i) a solid support component comprising magnesium halide, silica, modified silica, alumina, aluminum phosphate, or a mixture thereof, and (ii) a transition metal component represented by the formula: $TrX''_{hd u}(X''')_{v-u}$, or $TrX''_u O(X''')_{v-u-2}$ wherein:

Tr is a Group 4, 5, or 6 metal,

O is oxygen,

X" is halogen,

X'" is independently selected from hydrocarbyl, silyl, hydrocarbyloxy or siloxy having up to 10 non-hydrogen atoms, u is a number from 0 to 6 that is less than or equal to v, and v is the formal oxidation number of Tr.

These polymerizations are generally carried out under solution conditions to facilitate the intimate mixing of the two polymer-containing streams. The foregoing technique allows for the preparation of ethylene/α-olefin interpolymer compositions having a broad range of molecular weight distributions and composition distributions. Preferably, the heterogeneous catalyst is also chosen from those catalysts which are capable of efficiently producing the polymers under high temperatures, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition comprising the metal complex of the present invention with at least one of the aforementioned activating cocatalysts to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:

(i) a solid support component comprising a magnesium halide, silica or modified silica, including calcined silica, and (ii) a transition metal component represented by the formula: $TrX''_u(X''')_{v-u}$, or $TrX''_uO(X''')_{v-u-2}$ wherein: Tr, X'', X''', O, u, and v are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{3-8}$ α-olefins, most desirably 1-octene.

The skilled artisan will appreciate that the invention disclosed herein may be practiced in the absence of any component which has not been specifically disclosed. The following examples are provided as further illustration thereof and are not to be construed as limiting. Unless stated to the contrary all parts and percentages are expressed on a weight basis.

EXAMPLE 1

(N-t-butylamido)(dimethyl)(6,6-dimethyl-$\eta^5$-cyclohexadien-3-yl)silanetitanium (IV) dichloride 1. Preparation of 5,5-dimethyl- 1,3-cyclohexadiene/3,3-dimethyl- 1,4-cyclohexadiene isomeric mixture In a glass flask under nitrogen atmosphere, 50.0 g (0.357 mol) 5,5dimethyl-1,3-cyclohexanedione (dimedone) was slurried in about 500 mL of diethyl ether. After cooling the slurry in an ice bath, 13 g (0.342 mol) of LiAlH$_4$ was slowly added. The reaction mixture was allowed to warm to room temperature and was stirred for 2 hours, after which 14 g (0.369 mol) of additional LiAlH$_4$ was added. The reaction mixture was refluxed for 2 hours, then stirred overnight. Workup occurred as follows: After the reaction mixture was cooled in an ice bath, 27 mL of water was slowly added, followed by 27 mL of 15 weight percent, aqueous NaOH solution, then 81 mL of water. The resulting solids were filtered off and washed with diethyl ether. The combined ether solutions were concentrated by evaporation. To the resulting pale yellow product was added 10 mL of 9M aqueous H$_2$SO$_4$. The product was collected after distillation using a short path distillation column up to a pot temperature of 145° C. Additional H$_2$SO$_4$ was added and a second distillation was performed. After washing with 10 weight percent, aqueous Na$_2$CO$_3$, then with water, the product was dried with anhydrous MgSO$_4$. The product was fractionally distilled, with fractions boiling up to about 100° C. being collected. The yield was 12 g. of the isomeric mixture depicted as follows:

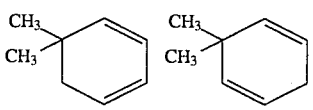

2. Preparation of potassium 6,6-dimethylcyclohexadienide

To 14.0 g (0.111 mol) of potassium t-amylate (KOC(CH$_3$)$_2$C$_2$H$_5$) in 200 mL of pentane was added 44.4 mL of 2.5M (0.111 mol) butyl lithium in hexane with formation of a small amount of brownish insoluble material. To this was added 12.0 (0.111 mol) of the dimethylcyclohexadiene isomeric mixture. A bright orange product resulted. After stirring overnight, the color became brownish orange. The product was filtered, washed several times with pentane, then dried under reduced pressure. The yield of orange powder was 11.8 g, 72.7 percent.

3. Preparation of (N-t-butylamino)(dimethyl)(4,4-dimethyl-2,5-cyclohexadien-1-yl)silane To a solution of 5.46 g (32.9 mmol) of ClSi(CH$_3$)$_2$NHC(CH$_3$)$_3$ (obtained according to the technique of EP-A-563,365) in tetrahydrofuran (THF) was slowly added 4.50 g (30.8 mmol) of solid potassium 6,6-dimethylcyclohexadienide. After stirring overnight, the reaction mixture was filtered and the solvent was removed under reduced pressure. The residue was extracted with pentane, the resulting slurry was filtered and the solvent was removed from the filtrate. Purification by Kugelrohr distillation gave 3.58 g of product, 49.0 percent yield. $^1$H NMR (C$_6$D$_6$)δ 5.69 (d, 10.2 Hz, 2H), 5.45 (d, 9.9 Hz, 2H), 2.30 (s, 1H), 113 (s, 3H), 1.12 (s, 3H), 1.07 (s, 9H), 0.12 (s, 6H). The structure of the product is depicted as follows:

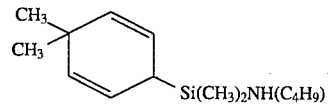

4. Preparation of dilithium(N-t-butylamido)(dimethyl)(4,4-dimethyl-$\eta^5$-cyclohexadien-1-yl)silane To 3.58 g (15.1 mmol) of (N-t-butylamino)(dimethyl)(4,4-dimethyl-2,5-cyclohexadien-1-yl)silane in 75 mL of diethyl ether was added 12.6 mL of 2.52M n-butyl lithium in hexane. The resulting yellow reaction solution was stirred for several days, during which time a large amount of precipitate had formed. The reaction mixture was refluxed for several hours, then it was filtered. The solid was washed with hexane and then dried under reduced pressure. The yield of the pale yellow powder was 2.01 g, 53.5 percent yield.

5. Preparation of (N-t-butylamido)(dimethyl)(6,6-dimethyl-$\eta^5$-cyclohexadien-3-yl)silanetitanium (IV) dichloride Dilithium(N-t-butylamido)(dimethyl)(4,4-dimethyl-$\eta^5$-cyclohexadien-1-yl)silane (1.11 g, 4.43 mmol) and 1.48 g (4.43 mmol) of TiCl$_4$.(THF)$_2$ were combined in 100 mL of diethyl ether. A dark brown solution formed immediately. After stirring overnight at room temperature, the reaction mixture was a dark brownish red. The mixture was filtered, the solvent was removed under reduced pressure, and the residue was extracted with hexane. After filtering, the solvent was removed from the filtrate under reduced pressure. A small amount of pentane was added to dissolve the viscous product. After recrystallizing overnight in the freezer, the supernatant was removed. The yield of deep red-black crystals was 0.054 g, 3.5 percent yield. $^1$H NMR (C$_6$D$_6$)δ 5.60 (s, 4H), 1.43 (s, 9H), 1.03 (s, 3H), 0.66 (s, 3H), 0.06 (s, 6H). $^{13}$C NMR(CC$_6$D$_6$)δ 133.4, 126.9, 103.6, 94.1, 61.2, 34.7, 32.3, 31.1, −0.7. The structure of the resulting product is as follows:

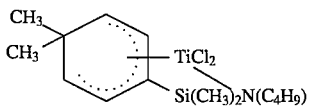

EXAMPLE 2

1. (N-t-butylamido)(dimethyl)(4,4-dimethyl-η$^5$-1,3-cyclohexadien-1-yl)-silanezirconium (IV) dichloride Dilithium(N-t-butylamido)(dimethyl)(4,4-dimethyl-η$^5$-cyclohexadien-1-yl)silane, 0.884 g (3.55 mmol) and 0.828 g (3.55 mmol) of ZrCl$_4$ were combined in 40 mL of toluene. A dark brown solution formed immediately. After five minutes, 5 mL of diethyl ether were added. After stirring overnight at room temperature, the reaction mixture was red-brown. The mixture was filtered, the solvent was removed under reduced pressure, and the residue was extracted with hexane. After filtering, the solvent was removed from the filtrate under reduced pressure. The product was recrystallized from a minimum amount of hexane at −40° C. to yield a brownish yellow solid. The yield was 0.4378 g, 31.0 percent. $^1$H NMR (C$_6$D$_6$)δ 5.63 (d, 8.0 Hz, 2H), 5.06 (d, 8.0 Hz, 2H), 1.33 (s, 9H), 1.11 (s, 3H), 0.64 (s, 3H), 0.14 (s, 6H). $^{13}$C NMR (C$_6$D$_6$)δ 1.30.1, 127.5, 117.0, 83.1, 56.3, 34.1, 33.1, 31.4, 0.4.

EXAMPLE 3

((N-t-butylamido)(dimethyl)(4,4-dimethyl-η$^5$-cyclohexadien-1-yl)silane])titanium (IV) dimethyl 0.049 g Of (N-t-butylamido)(dimethyl)(4,4-dimethyl-η$^5$-cyclohexadien-1-yl)silane titanium dichloride (0.12 mmol) was dissolved in 10 mL of diethyl ether. To this solution 0.08 mL of magnesium methyl iodide (CH$_3$MgI) (3.0M in THF) was added dropwise at 25° C. with stirring over a 20 min period. Upon completion of the addition of the CH$_3$MgI the solution was stirred for 20 minutes. After this time period the diethyl ether was removed under reduced pressure and the residue extracted with pentane. The solution was then filtered, the filtrate was evaporated to dryness under reduced pressure to give 0.026 g (66 percent yield) of the desired product. $^1$H NMR (C$_6$D$_6$): δ 5.25 (d, 2H), 5.05 (d, 2H), 1.46 (s, 9H), 1.32 (s 6H), 1.18 (s, 3H), 0.66 (s, 3H), 0.20 (s, 6H).

Polymerization Examples

A two liter stirred reactor was charged with approximately 740 g of mixed alkane solvent (Isopar-E™ available from Exxon Chemicals Inc.) (sol) and about 120 g of 1-octene comonomer (C$_8$). Hydrogen (approximately Δ25 psi, 170 kPa) was added to the reactor by differential pressure expansion from a 75 mL addition tank initially at 2070 kPa. The reactor was heated to 140° C. and saturated with ethylene at 3450 kPa. Catalyst and cocatalyst were mixed in a dry box by pipetting the indicated amount of 1.5M solution of methylalumoxane (MAO) used as cocatalyst in toluene into a 0.005M solution of the catalyst in toluene. The resulting solution was transferred to a catalyst addition tank and injected into the reactor. The extent of reaction is indicated by the maximum temperature rise caused by the exothermic reaction (exo). The polymerization was allowed to proceed with ethylene being added on demand. After 15 minutes the polymer solution was removed from the reactor. A hindered phenol antioxidant (Irganox™ 1010 available from Ciba Geigy Corp.) was added to the resulting ethylene/1-octene copolymers in the amount of 100 mg per batch. Volatiles were removed from the polymers under reduced pressure in an oven at about 120° C. for approximately 20 hours. Melt index (MI), where performed, was conducted by a calibrated micro melt index machine due to the small sample size, yielding a melt index that is equivalent to values determined according to ASTM-1238, Condition G. Run conditions and the results are found in Table I.

EXAMPLE 4

(N-t-butylamido)(dimethyl)(2,4-dimethyl-η$^5$-pentadien-1-yl)silanezirconium (IV) dichloride 1. Preparation of (N-t-butylamino)(dimethyl)(2,4-dimethyl-2,4-pentadien-1-yl)silane To a solution of 0.612 g (3.69 mmol) of (N-t-butylamino)(chloro)dimethylsilane in 50 mL of THF was added 0.500 g (3.72 mmol) of potassium 2,4-dimethylpentadienide (prepared in a manner similar to that reported in *J. Am. Chem. Soc.* 1978, 100, 3258). The reaction mixture was stirred overnight. The solvent was removed, the residue was extracted with pentane and filtered. The pentane was removed in vacuo to give the product as a pale yellow oil. The yield was 0.733 g, 88.2 percent. $^1$H NMR (C$_6$D$_6$) δ 5.64 (s, 1H), 5.01 (s, 1H), 4.97 (s, 1H), 1.88(s, 2H), 1.85(s, 3H), 1.76(s, 3H), 1.09(s, 9H), 0.17 (s, 6H). $^{13}$C NMR (C$_6$D$_6$) δ 142.7, 136.5, 125.3, 113.2, 49.5, 34.0, 27.9, 26.5, 24.6, 2.8.

TABLE I

| Run | sol (g) | 1-octene (g) | catalyst (μmol) | cocatalyst (μmol) | yield (g) | MI dg/min |
|---|---|---|---|---|---|---|
| 1 | 747 | 123 | Ex. 1 (2.0) | MAO (2000) | 7.7 | — |
| 2 | 740 | 123 | Ex. 1 (3.0) | MAO (3000) | 10.8 | 1.92 |
| 3 | 740 | 120 | Ex. 2 (2.0) | MAO (2000) | 10.7 | — |
| 4 | 740 | 126 | Ex. 2 (4.0) | MAO (4000) | 19.2 | 436 |
| 5 | 740 | 123 | Ex. 3 (2.0) | B(C$_6$F$_5$)$_3$ (6)[1] | 3.2 | — |
| 6 | 750 | 129 | Ex. 3 (2.0) | Ph$_3$C + B(C$_6$F$_5$)$_4^-$ (2)[2] | 9.4 | — |
| 7 | 744 | 126 | Ex. 3 (2.0) | Et$_3$Si + B(C$_6$F$_5$)$_4^-$ (2)[3] | 8.2 | — |
| 8 | 747 | 117 | Ex. 3 (3.0) | C$_6$F$_5$OH.B(C$_6$F$_5$)$_3$ (3)[4] | 2.6 | — |

[1]. trispentafluorophenylborane
[2]. triphenylcarbenium tetrakispentafluorophenylborate
[3]. triethylsilylium tetrakispentafluorophenylborate prepared by reaction of triethylsilane chloride with triphenylcarbenium tetrakispentafluorophenylborate in toluene solution. The procedure is analogous to that disclosed in J. Chem Soc. Chem. Comm., 1993, 383–384, as well as Lambert, J. B., et al., Organometallics, 1994, 13, 2430–2443
[4]. pentafluorophenol trispentafluorophenylborane adduct prepared by combining equal molar quantities of trispentafluorophenylborane and pentafluorophenol in toluene.

2. Preparation of dilithium (N-t-butylamido)(dimethyl)(2,4-dimethyl-2,4-pentadien-1-yl)silane To a magnetically stirred solution of 5.92 g (26.3 mmol) of (N-t-butylamino)(dimethyl)(2,4-dimethyl-2,4-pentadien-1-yl)silane in 40 mL of Et$_2$O was added 39.6 mL of 1.36M (53.9 mmol) n-butyl lithium in hexane. A Precipitate gradually formed until the reaction mixture became too thick for efficient stirring. Additional diethyl ether was added to bring the reaction volume up to about 100 mL. The reaction mixture was stirred overnight. A white precipitate was filtered from a yellow solution. The solid was washed with diethyl ether. The yield of the product as a mono ether adduct (by NMR) was 2.558 g, 31.3 percent.

3. Preparation of (N-t-butylamido)(dimethyl)(2,4-dimethyl-η$^5$-pentadien- 1-yl)silanezirconium (IV) dichloride A reaction mixture of 0.845 g (2.71 mmol) of dilithium (N-t-butylamido)(dimethyl)( 2,4-dimethyl-2,4-pentadien-3-yl)silane and 0.8295 g (3.56 mmol) of ZrCl$_4$ in 65 mL of toluene was stirred for several days, then filtered. The solvent was removed from the red-brown solution under reduced pressure, the residue was extracted with diethyl ether, then filtered and the solvent was removed to give a red-brown solid, which was extracted with pentane and isolated to give a dark red-brown liquid which solidified on standing.

EXAMPLE 5

(N-t-butylamido)(dimethyl)(2,4-dimethyl-η$^5$-pentadien-1-yl)silanetitanium (IV) dichloride 1. Preparation of (N-t-butylamido)(dimethyl)(2,4-dimethyl-η$^5$-pentadien-1-yl)silanetitanium (III) chloride (THF adduct)

A reaction mixture was formed by combining 0.862 g (2.77 mmol) of dilithium (N-t-butylamido)(dimethyl)(2,4-dimethyl-2,4-pentadien-1-yl)silane and 1.35 g (3.63 mmol) of TiCl$_3$.3THF in 50 mL of THF. After stirring overnight, the solution was filtered, the solvent was removed under reduced pressure, the residue was extracted with pentane, the dark solution was filtered and then concentrated and chilled in a –35° C. freezer. The brown solid product was isolated.

2. Preparation of (N-t-butylamido)(dimethyl)(2,4,dimethyl-η$^5$-pentadien-1-yl)silanetitanium (IV) dichloride A reaction mixture was formed by combining 0.85 g (2.73 mmol) of dilithium (N-t-butylamido)(dimethyl)(2,4-dimethyl-η$^5$-pentadien-1-yl)silane and 1.33 g (3.59 mmol) of TiCl$_3$.3THF in 50 mL of THF. To the reaction mixture was then added 0.500 g (18.0 mmol) of PbCl$_2$. After stirring overnight, the solution was filtered, the solvent was removed under reduced pressure, the residue was extracted with toluene, the solution was filtered and the solvent was removed. The residue was then extracted with pentane, the solution was filtered and then concentrated and chilled in a –35° C. freezer. A red-orange solid product was isolated.

EXAMPLE 6

(N-t-butylamido)(diphenyl)(2,4-dimethyl-η$^5$-pentadien-1-yl)silanetitanium (IV) dichloride 1. Preparation of (N-t-butylamino)(diphenyl)(2,4-dimethyl-2,4-pentadien-1-yl) silane To a solution of 0.3238 g (1.12 mmol) of (N-t-butylamino)(chloro)diphenylsilane in 50 mL of THF was added 1.500 g (1.12 mmol) of potassium 2,4-dimethylpentadienide. The reaction mixture was stirred overnight. The solvent was removed, the residue was extracted with pentane and filtered. The pentane was removed in vacuo to give the product as a pale yellow oil. The yield was 0.3633 g 93.0%. $^1$H NMR (C$_6$D$_6$) δ 7.79 (m, 4H), 7.22 (m, 6H), 5.65 (s, 1H), 5.08 (s, 1H), 4.98 (s, 1H), 2.44 (s, 2H), 1.84 (s, 3H), 1.57 (s, 3H), 1.30 (s, 1H), 1.09(s, 9H), (s, 6H). $^{13}$C NMR(C$_6$D$_6$)δ 142.7, 138.5, 136.0, 135.8, 129.6, 128.0, 126.5, 113.7, 50.2, 33.9, 27.9, 25.1, 24.5

2. Preparation of dilithium(N-t-butylamido)(diphenyl)(2,4-dimethyl-2,4-pentadien-1-yl)silane (N-t-butylamino)(diphenyl)(2,4-dimethyl-2,4-pentadien-1-yl)silane is combined in diethyl ether with a sufficient quantity of 2.5M n-butyl lithium in hexane to provide a molar ratio of silane:lithium of at least 1:2. The resulting solution is then stirred for several days, followed by refluxing for several hours. The reaction mixture is filtered and the resulting solid is washed with hexane and then dried under reduced pressure.

3. Preparation of (N-t-butylamido)(diphenyl)(2,4-dimethyl-η$^5$-pentadien-1-yl)silanetitanium (IV) dichloride Dilithium(N-t-butylamido)(diphenyl)(4,4-dimethyl-2,4-pentadien-1-yl)silane and TiCl$_4$.(THF)$_2$ are combined in equal molar amounts in 100 mL of diethyl ether. After stirring overnight at room temperature, the reaction mixture is filtered, the solvent is removed under reduced pressure, and the residue is extracted with hexane. After filtering, the solvent is removed from the filtrate under reduced pressure. Recrystallizing from –35° C. pentane results in isolation of the desired product.

EXAMPLE 7

(N-t-butylamido)(dimethyl)(1,5-bis(trimethylsilyl)-2,4-dimethyl-η$^5$-pentadien-3-yl)silanetitanium (IV) dichloride 1. Preparation of 1-(trimethylsilyl)-2,4-dimethyl-2,4-pentadiene A solution of 15.1 g (112 mmol) of potassium 2,4-dimethylpentadienide in 250 mL of THF was added to a –35° C. solution of 36.0 g (33.1 mmol) of trimethylsilyl chloride in 200 mL of THF. The yellow-orange color of the pentadienyl anion faded instantly upon addition. The reaction mixture was stirred overnight. The solvent was removed under reduced pressure, the residue was extracted with pentane, the resulting solution was filtered from insolubles and concentrated under reduced pressure to give the product as a pale yellow liquid. The yield was 11.65g, 61.5%. $^1$H NMR(C$_6$D$_6$) δ 5.63 (s, 1H), 4.95 (s, 1H), 4.92 (s, 1H), 1.83 (s, 3H), 1.81 (s, 2H), 1.68 (s, 3H), 0.03 (s, 9H). $^{13}$C NMR (C$_6$D$_6$) δ 142.5, 136.0 125.2, 113.1, 27.8, 24.5, –0.2.

2. Preparation of lithium (1-(trimethylsilyl)-2,4-dimethylpentadienide).

In a manner similar to that found in Organometallics 1983, 2, 21, 11.6 g (69.2 mmol) of 1-(trimethylsilyl)-2,4-dimethyl-2,4-pentadiene in 15 mL of THF was added dropwise to 27.4 mL of a 2.52M (69.1 mmol) hexane solution of butyl lithium in 40 mL of THF at about –10° to 0° C. The reaction mixture was stirred overnight. The solvents were removed under reduced pressure. The pasty orange solid was washed twice with 30 mL of heptane, collected on a frit, washed with pentane, then dried under reduced pressure. The yield of light yellow powder was 3.61 g, 29.9 percent.

3. Preparation of 1,5-bis(trimethylsilyl)-2,4-dimethyl-1,3-pentadiene

To a solution initially at –35° C. of 3.609 g (20.7 mmol) of lithium (1-(trimethylsilyl)- 2,4-dimethylpentadienide) in 30 mL of THF was added about 5 g (~46 mmol) of trimethylsilyl chloride. Copious precipitate formed immediately. After stirring overnight, the solvent was removed and the residue was extracted with pentane. After filtering, the solvent was removed under reduced pressure to give the product as a pale yellow liquid. The yield was 4.05 g, 81.3 percent. Major isomer: $^1$H NMR (C$_6$D$_6$) δ 5.72 (s, 1H), 5.50 (s, 1H), 1.88 (s, 3H), 1.85 (s, 2H), 1.69 (s, 3H), 0.20 (s, 9H), 0.06 (s, 9H). $^{13}$C NMR (C$_6$D$_6$) δ 151.8, 135.6, 128.9, 126.4, 27.8, 24.6, 23.5, 0.7, −0.2.

4. Preparation of lithium (1,5-bis(trimethylsilyl)-2,4-dimethylpentadienide)

To a solution of 4.05 g (16.8 mmol) of 1,5-bis(trimethylsilyl)-2,4-dimethyl-1,3-pentadiene in 30 mL of THF was added 6.68 mL of 2.52M (16.8 mmol) n-butyl lithium in hexane. The resulting reaction mixture was stirred overnight, after which the solvents were removed under reduced pressure. After stirring with pentane, the resulting slurry was filtered. The solids, washed with pentane and dried under reduced pressure, were identified as lithium (1-(trimethylsilyl)-2,4-dimethylpentadienide). The solvent was removed from the filtrate to give lithium (1,5-bis(trimethylsilyl)-2,4-dimethylpentadienide)(THF)$_{1.5}$. The yield was 4.00 g 67.0%. $^1$H NMR (C$_6$D$_6$)d 4.64 (s, 1H), 4.41 (s, 2H), 3.23 (br m, 6H) 2.17 (s, 6H), 1.15 (br m, 6H), 0.35 (s, 18H). $^{13}$C NMR (C$_6$D$_6$) δ 152.2, 94.3, 83.9, 68.7, 28.1, 25.5, 2.7.

5. Preparation of 1,5-bis(trimethylsilyl)-2,4-dimethyl-3-(N-t-butylaminodimethylsilyl)- 1,4-pentadiene To a solution of 4.00 g (11.3 mmol) of lithium (1,5-bis(trimethylsilyl)-2,4-dimethylpentadienide)(THF)$_{1.5}$ in 40 mL of diethyl ether cooled to −35° C. was added 2.69 g (16.2 mmol) of tert-butylaminochlorodimethylsilane. A precipitate formed as the reaction mixture was allowed to warm to ambient temperature. The reaction mixture was stirred overnight. The solvent was removed and the residue was extracted with pentane and filtered. The pentane was removed in vacuo to give the product.

6. Preparation of dilithium(N-t-butylamido)(dimethyl)(1,5-bis(trimethylsilyl)- 2,4-dimethyl-1,4-pentadien-3-yl)silane 1,5-bis(trimethylsilyl)-2,4-dimethyl-3-(N-t-butylaminodimethylsilyl)-1,4-pentadiene is combined in diethyl ether with a sufficient quantity of 2.5M n-butyl lithium in hexane to provide a molar ratio of silane:lithium of at least 1:2. The resulting solution is then stirred for several days, followed by refluxing for several hours. The reaction mixture is filtered and the resulting solid is washed with hexane and then dried under reduced pressure.

7. Preparation of (N-t-butylamido)(dimethyl)(1,5-bis(trimethylsilyl)-2,4-dimethyl-η$^5$-pentadien- 3-yl)silanetitanium (IV) dichloride Dilithium(N-t-butylamido)(dimethyl)(1,5-bis(trimethylsilyl)-2,4-dimethyl-1,4-pentadien-3-yl)silane and TiCl$_4$.(THF)$_2$ are combined in equal molar amounts in 100 mL of diethyl ether. After stirring overnight at room temperature, the reaction mixture is filtered, the solvent is removed under reduced pressure, and the residue is extracted with hexane. After filtering, the solvent is removed from the filtrate under reduced pressure. Recrystallizing from −35° C. pentane results in isolation of the desired product.

EXAMPLE 8

(N-t-butylamido)(dimethyl)(6,6-dimethyl-η$^5$-cyclohexadien-3-yl)silanetitanium (IV) dichloride A 250 mL flask was charged with TiCl$_3$(THF)$_3$ (2.23 g, 6.01 mmol) and 125 mL of THF. A THF solution of dilithium(N-t-butylamido)(dimethyl)(4,4-dimethyl-η$^5$-1,3-cyclohexadien-1-yl)silane (prepared according to example 1, step 4) (1.50 g, 6.01 mmol) was then added via a constant addition funnel over a 5 minute period at 25° C. to give a dark brown opaque mixture. PbCl$_2$ (1.80 g, 6.48 mmol) was added as a solid at 25° C. and the resulting mixture stirred for 2 hours. The volatiles were removed under reduced pressure and the solid triturated once with hexane. Hexane (50 mL) was then added and the mixture filtered through Celite™ diatomaceous earth filter aid, to give a dark brown solution. Concentration of the solution to 30 mL, cooling to −78° C., and filtration gave brown crystals of the desired product. Yield was 1.01 g, 47 percent.

Polymerization

A two liter stirred reactor was charged with 740 g of Isopar-E™ mixed alkanes solvent and 126 g of 1-octene. Hydrogen (approximately Δ25 psi, 170 kPa) was added to the reactor by differential pressure expansion from a 75 mL addition tank. The reactor was heated to 140° C. and saturated with ethylene at 3.4 MPa. Catalyst and cocatalyst were mixed in a dry box by combining 2.7 ml of a 1.5M toluene solution of methylaluminoxane (MAO) (4000 μmole) and 0.8 mL of a 0.005M toluene solution of the catalyst (4 μmole). The resulting solution was transferred to a catalyst addition tank and injected into the reactor. The polymerization was allowed to proceed with ethylene being added on demand. After 15 minutes the polymer solution was removed from the reactor. A hindered phenol antioxidant (Irganox™ 1010 available from Ciba Geigy Corp.), 100 mg, was added. Volatiles were removed under reduced pressure in an oven at about 120° C. for approximately 20 hours. Yield was 15.1 g of ethylene/1-octene copolymer having a melt index of 0.72 dg/min..

EXAMPLE 9

(N-t-butylamido)(dimethyl)(1,1-dimethyl-2, 3, 4, 9, 10-η-1,2-dihydronaphthalen-4-yl)silanetitanium (IV) dichloride 1. Preparation of potassium 4,4-dimethyldihydronaphthalide A mixture of 4,4-dimethyl-3,4-dihydronaphthalene and 4,4-dimethyl-1,4-dihydronaphthalene (83:17 ratio, 6.00 g, 37.9 mmol) was dissolved in approximately 200 mL of hexane in a 250 mL flask. To the flask was added potassium amylate (4.91 g, 38.9 mmol) followed by n-BuLi (16.1 mL, 2.48M, 39.8 mmol). Immediate formation of an orange solid resulted. After stirring for 1 hour, the slurry was filtered and the solid washed four times with 20 mL of hexane each time. The solid was transferred to a flask which was evacuated to remove any volatiles. The desired product was recovered as a powdery orange solid. Yield was 6.91 g, 93 percent.

2. Preparation of (dimethyl)(N-t-butylamino)(4,4-dimethyldihydronaphthalen-1-yl)silane A 500 mL flask was charged with dimethyl(t-butylamino)chlorosilane (ClSiMe$_2$NH$^t$Bu) (5.81 g, 35.1 mmol) and approximately 80 mL of THF. A constant addition funnel was attached containing the potassium 4,4-dimethyldihydronaphthalide complex of step 1 (4.00 g, 20.4 mmol) dissolved in about 120 mL of THF. The flask was cooled to −78° C. and the orange solution added dropwise over a 3 hour period. The bath was removed and the mixture allowed to warm to 25° C. during which the color changed from tan to yellow. The solvent was removed under reduced pressure and the residue triturated once with 80 mL of hexane. The residue was taken up in hexane and filtered through Celite™ brand diatomaceous earth filter aid. The solids were washed once with 20 mL of hexane and the combined filtrates were concentrated. Stirring overnight under reduced pressure resulted in a yellow oil. Yield was 4.72 g, 80 percent.

3. Preparation of dilithium(dimethyl)(N-t-butylamido)(4,4-dimethyldihydronaphthalen-1-yl)silane A 250 mL flask was charged with the (dimethyl)(N-t-butylamino)(4,4-dimethyldihydronaphthalenyl)silane mixture of step 2 (4.72 g, 16.4 mmol) and 120 mL of diethyl-ether. To this solution was added sec-BuLi (25.9 mL, 1.3M, 33.6 mmol) in small aliquots via syringe through a septum at 25° C. The yellow-orange mixture was stirred overnight. The reaction mixture was filtered though Celite™ brand diatomaceous earth filter aid, the ether was removed and the residue triturated with hexane three times and discarded. The hexane was removed by evaporation and diethylether was added. This mixture was stirred overnight during which time a solid formed. The yellow solid flocculent material was isolated by filtration and dried in vacuo. Yield was 0.66 g, 13 percent.

4. Preparation of (N-t-butylamido)(dimethyl)(1,1-dimethyl-2, 3, 4, 9, 10-η- 1,4-dihydronaphthalen-4-yl)silanetitanium (IV) dichloride If (dimethyl)(N-t-butylamino)(4,4-dimethyldihydronaphthalen-1-yl)silane dilithium and $TiCl_4 \cdot (THF)_2$ are combined in equimolar amounts in diethyl ether solvent, at room temperature for about one day, the reaction mixture filtered, the solvent removed under reduced pressure, and the residue extracted with hexane, the desired product may be recovered by filtration followed by solvent removal under reduced pressure.

EXAMPLE 10

(N-t-butylamido)(dimethyl)(4,4-dimethyl-$\eta^5$-cyclohexadien-1-yl)silanetitanium (II) (1,4-diphenylbutadiene)

A 100 mL flask was charged with (N-t-butylamido)(dimethyl)(4,4-dimethyl-$\eta^5$-cyclohexadien-1-yl)silanetitanium (IV) dichloride (200 mg, 0.565 mmol), prepared according to Example 1, and about 50 mL of hexane. To this solution was added trans,trans-1,4-diphenylbutadiene (116 mg, 0.565 mmol) followed by n-BuLi (0.455 mL, 2.48M, 1.13 mmol). The brown solution was refluxed for 1 h, cooled to 25° C., and filtered through Celite™ brand diatomaceous earth filter aid. The volume was reduced and the solution cooled to −25° C. overnight. Brown microcrystals were isolated by filtration. Yield was 75 mg, 27 percent.

Polymerization 1

A two liter stirred reactor was charged with 752 g of Isopar-E™ mixed alkanes solvent and 110 g of 1-octene. Hydrogen (approximately Δ28 psi, 190 kPa) was added to the reactor by differential pressure expansion from a 75 mL addition tank. The reactor was heated to 140° C. and saturated with ethylene at 3.4 MPa. Catalyst and cocatalyst were mixed in a dry box by combining 0.6 mL of a 0.005M toluene solution of (N-t-butylamido)(dimethyl)(4,4-dimethyl-$\eta^5$-cyclohexadien-1-yl)silanetitanium (II) (1,4-diphenylbutadiene) (3.0 μmole) and 9.0 μmole of tris(pentafluorophenyl)borane also in toluene. The resulting solution was transferred to a catalyst addition tank and injected into the reactor. The polymerization was allowed to proceed with ethylene being added on demand. After 10 minutes the polymer solution was removed from the reactor. A hindered phenol antioxidant (Irganox™ 1010 available from Ciba Geigy Corp.), 100 mg, was added. Volatiles were removed under reduced pressure in an oven at about 130° C. for approximately 18 hours. Yield was 5.9 g of ethylene/1-octene copolymer.

Polymerization 2

The above polymerization conditions were substantially repeated using 701 g of Isopar-E™ mixed alkanes solvent and 1156 g of 1-octene. Hydrogen (approximately Δ28 psi, 190 kPa) was added to the reactor by differential pressure expansion from a 75 mL addition tank. The reactor was heated to 100° C. and saturated with ethylene at 3.4 MPa. Catalyst and cocatalyst were mixed in a dry box by combining 3.0 μmole of (N-t-butylamido)(dimethyl)(4,4-dimethyl-$\eta^5$-cyclohexadien- 1-yl)silanetitanium (II)(1,4-diphenylbutadiene) and 9.0 μmole of tris(pentafluorophenyl)borane. The resulting solution was transferred to a catalyst addition tank and injected into the reactor. The polymerization was allowed to proceed with ethylene being added on demand. After 10 minutes the polymer solution was removed from the reactor. A hindered phenol antioxidant (Irganox™ 1010 available from Ciba Geigy Corp.), 100 mg, was added. Volatiles were removed under reduced pressure in an oven at about 130° C. for approximately 18 hours. Yield was 4.0 g of ethylene/1-octene copolymer.

EXAMPLE 11

(N-t-butyl amido)(dimethyl)(4,4-dimethyl-$\eta^5$-cyclohexadien-3-yl)silanetitanium pentadiene A flask was charged with 300 mg (0.847 mmol) of (N-t-butylamido)(dimethyl)( 4,4-dimethylcyclohexadienyl-)silanetitanium dichloride, 1.15 g (16,9 mmol) of 1,3-pentadiene, and 50 mL of hexane. To this solution was added n-BuLi via syringe in one portion (0.68 mL, 2.50M in hexane, 1.69 mmol). The brown solution was refluxed for 1 hour and upon cooling, filtered through Celite™ brand dietomaceous earth filter aid. The volatiles were removed to give a brown solid which was identified by $^1$H NMR as the pentadiene complex.

EXAMPLE 12

(Dimethyl)(N-t-butylamido)(diphenylmethyl)-silanetitanium (IV) dichloride

Preparation of diphenylmethyl potassium

To a solution of 18.3 g (109 mmol) of diphenylmethane in 400 mL of hexane were added 11.99 g (109 mmol) of potassium t-amylate. To the resulting pale yellow solution were added 68.75 mL of 1.60M (110 mmol) butyl lithium. The thick, bright orange slurry was stirred overnight. The solids were collected on a filter, washed three times with 100 mL, then twice with 50 mL of hexane, then dried under reduced pressure. The yield of bright orange powder was 18.23 g, 81.2 percent.

Preparation of (N-t-butylamino)(dimethyl)(diphenylmethyl)silane

To a solution of 4.1 g (24.7 mmol) of ClSiMe2NHCMe3 in 80 mL of THF were added 3.735 g (18.1 mmol) of solid diphenylmethyl potassium. The orange color of the diphenylmethyl potassium disappeared instantly and precipitate formed rapidly. The reaction mixture was stirred for several days. The solvent was removed under reduced pressure and the residue was extracted with hexane and the solvent was removed under reduced pressure. The yellow liquid product was subjected to vacuum pumping to remove the excess ClSiMe$_2$NHCMe$_3$. The yield was 4.786 g, 88.9 percent.

$^1$H NMR, (CDCl$_3$) δ 7.33–7.06 (br, m, 10H), 3.57 (s, 1H), 1.22 (s, 1H), 1.06 (s, 9H), 0.08 (s, 6H). $^{13}$C NMR, (CDCl$_3$) δ 142.8, 128.9, 128.0, 124.8, 49.6, 47.4, 33.8, 1.3.

Preparation of dilithium(N-t-butylamido)(dimethyl)-(diphenylmethyl)silane

To a solution of 4.786 g (16.1 mmol) of (N-t-butylamino)(dimethyl)(diphenylmethyl)silane in 50 mL of ether were added 14.1 mL of 2.285M (32.2 mmol) of n-butyl lithium in hexanes. There was vigorous gas evolution and the is reaction solution darkened to an orange-red color. The reaction mixture was stirred overnight. The bright orange precipitate which had formed was filtered off, washed with hexane, then dried under vacuum. The yield of bright orange powder was 2.213 g, 44.5%. Additional butyl lithium solution (2–3mL) was added to the filtrate, which was then stirred for several days. More precipitate gradually formed. It was isolated as above to give 0.916 g additional product. Total yield was 3.129 g, 62.9 percent.

Preparation of (N-t-butylamido)(dimethyl)(diphenylmethyl)-silanetitanium (IV) dichloride Solid dilithium(N-t-butylamido)(dimethyl)(diphenylmethyl)silane (0.712 g, 2.30 mmol) was mixed with 0.853 g (2.30 mmol) of solid TiCl$_3$.3THF in a flask to which 50 mL of THF was then added. After allowing to stir for about 5 minutes, 0.640 g (2.30 mmol) of PbCl$_2$ was added to the deep red solution. The resulting orange-red reaction mixture was stirred overnight. The solvent was removed under reduced pressure, the residue was extracted with hexane, then filtered. The solution was concentrated to about 5 mL, then chilled overnight in a freezer for several days to maximize precipitation. The resulting solid material was separated by filtration, washed with cold hexane, then dried under reduced pressure. The yield of dark brown microcrystalline product was 0.515 g, 54.1 percent.

Polymerization

A two liter stirred reactor was charged with 750 g of Isopar E™ solvent and 110 g of 1-octene. The reactor was heated to 140° C. and saturated with ethylene at 3.4 MPa (500 psi). Catalyst and cocatalyst were mixed in a dry box by combining 0.6 mL of a 0.005M toluene solution of (N-t-butylamido)(dimethyl)(diphenylmethyl)silanetitanium (IV) dichloride (3.0 μmole) and 2.0 mL of a 1.5M toluene solution of methylalumoxane (3000 μmole). The resulting solution was transferred to a catalyst addition tank and injected into the reactor. The polymerization was allowed to proceed with ethylene being added on demand. After 10 minutes the polymer solution was removed from the reactor. A hindered phenol antioxidant (Irganox™ 1010 available from Ciba Geigy Corp.), 100 mg, was added. Volatiles were removed under reduced pressure in an oven at about 130° C. for approximately 18 hours. Yield was 1.1 g of ethylene/1-octene copolymer.

EXAMPLE 13

(N-t-butylamido)(dimethyl)(diphenylmethyl)-silanezirconium (IV) dichloride

To 0.528 g (2.26 mmol) of ZrCl$_4$ were added 6 mL of hexane, then 3 mL of diethyl ether, then 4 mL of THF. After the solvents were removed, solid dilithium(N-t-butylamido)(dimethyl)(diphenylmethyl)silane (0.700 g, 2.26 mmol) was mixed together with the zirconium complex after which 50 mL of toluene was added. The resulting brown reaction mixture was stirred for several days. The solution was filtered, then the solvent was removed under reduced pressure. The residue was extracted with hexane, then filtered. After concentrating, the solution was chilled for several days in a freezer to maximize precipitation. The resulting orange powder was separated by filtration, washed with cold hexane, then dried under reduced pressure. The yield was 0.332 g, 32.0 percent.

Polymerization

A two liter stirred reactor was charged with 750 g of Isopar E™ solvent and 107 g of 1-octene. The reactor was heated to 140° C. and saturated with ethylene at 3.4 MPa (500 psi). Catalyst and cocatalyst were mixed in a dry box by combining 0.6 mL of a 0.005M toluene solution of (N-t-butylamido)(dimethyl)(diphenylmethyl)silanezirconium (IV) dichloride (3.0 μmole) and 2.0 mL of a 1.5M toluene solution of methylalumoxane (3000 μmole). The resulting solution was transferred to a catalyst addition tank and injected into the reactor. The polymerization was allowed to proceed with ethylene being added on demand. After 10 minutes the polymer solution was removed from the reactor. A hindered phenol antioxidant (Irganox™ 1010 available from Ciba Geigy Corp.), 100 mg, was added. Volatiles were removed under reduced pressure in an oven at about 130° C. for approximately 18 hours. Yield was 1.3 g of ethylene/1-octene copolymer.

What is claimed is:

1. A metal complex corresponding to the formula:

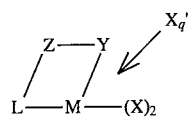

wherein:

M is a Group 4 metal in the +2 or +4 formal oxidation state;

L is a group containing a cyclic or noncyclic, non-aromatic, anionic, dienyl ligand group bound to M and Z, said L group containing up to 60 nonhydrogen atoms;

Z is a moiety covalently bound to both L and Y, comprising boron, or a member of Group 14 of the Periodic Table of the Elements, said moiety having up to 60 non-hydrogen atoms;

Y is a moiety comprising nitrogen, phosphorus, sulfur or oxygen through which Y is covalently bound to both Z and M, said moiety having up to 20 nonhydrogen atoms;

X' independently each occurrence is a Lewis base containing up to 40 nonhydrogen atoms;

X independently each occurrence is a monovalent anionic moiety having up to 20 non-hydrogen atoms, provided however that neither X is an aromatic group that is π-bonded to M; optionally, two X groups may be covalently bound together forming a divalent dianionic moiety having both valences bound to M; or two X groups together form a neutral, conjugated or nonconjugated diene that is π-bonded to M (whereupon M is in the +2 oxidation state); or further optionally one or more X and one or more X' groups may be bonded together thereby forming a moiety that is both covalently bound to M and coordinated thereto by means of Lewis base functionality; and q is a number from 0 to 3.

2. A metal complex according to claim 1 wherein L is a divalent derivative of a pentadienyl, cyclohexadienyl, cyclosilahexadienyl, cycloheptadienyl, or cyclooctadienyl groups; a hydrocarbyl, silyl, hydrocarbyloxy or siloxy substituted pentadienyl, cylohexadienyl, cyclosilahexadienyl, cycloheptadienyl or cyclooctadienyl group group; a partially hydrogenated anthracenyl, or partially hydrogenated naphthalenyl group; or a hydrocarbyl, silyl, hydrocarbyloxy or siloxy substituted partially hydrogenated anthracenyl or partially hydrogenated naphthalenyl group.

3. A metal complex according to claim 1 wherein L corresponds to the formula:

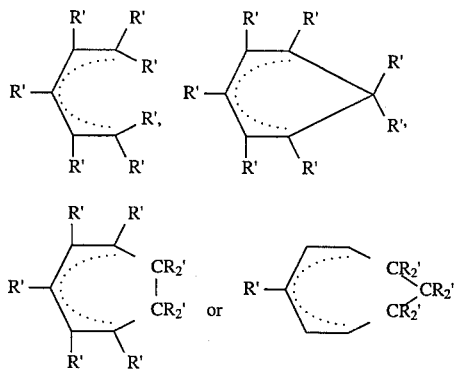

wherein:
wherein R' in each occurrence is a ligand that is independently selected from the group consisting of hydrogen, hydrocarbyl, silyl, germyl, siloxy, amino, hydrocarbyloxy, cyano, halo and combinations thereof, said R' having up to 20 non-hydrogen atoms, and optionally, two or more R' groups (where R' is not hydrogen, halo or cyano) may together form a divalent derivative of one of the foregoing ligands; and provided further that one R' comprises a covalent bond to Z.

4. A metal complex according to claim 1 corresponding to the formula:

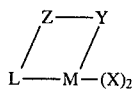

wherein:
Y is —O—, —S—, —NR*—, —PR*—;
Z is $SIR^*_2$, $CR^*_2$, $SiR^*_2SiR^*_2$, $CR^*_2CR^*_2$, $CR^*=CR^*$, $CR^*_2SiR^*_2$, $CR^*_2CR^*_2CR^*_2$, $CR^*_2SiR^*_2CR^*_2$, $SiR^*_2CR^*_2CR^*_2$, $SiR^*_2CR^*_2SiR^*_2$, $SiR^*_2SiR^*_2CR^*_2$, $SiR^*_2SiR^*_2SiR^*_2$, or $GeR^*_2$; wherein:
R* each occurrence is independently hydrogen, or a member selected from the group consisting of from hydrocarbyl, silyl, halogenated alkyl, halogenated aryl, and combinations thereof, said R* having up to 18 nonhydrogen atoms, and optionally (when R* is not hydrogen), two R* groups from Z, or an R* group from Z and an R* group from Y form a ring system;

M is titanium or zirconium in the +2 or +4 formal oxidation state;

L is a divalent derivative of a pentadienyl, cyclohexadienyl, cyclosilahexadienyl, partially hydrogenated naphthalenyl, partially hydrogenated anthracenyl group or a hydrocarbyl, hydrocarbyloxy, silyl or siloxy substituted pentadienyl, cyclohexadienyl, cyclosilahexadienyl, partially hydrogenated naphthalenyl, or partially hydrogenated anthracenyl group, each said hydrocarbyl, hydrocarbyloxy, silyl or siloxy substituent having up to 10 nonhydrogen atoms; and x is chloro, hydrocarbyl, hydrocarbyloxy or an N, N-dialkylamino substituted hydrocarbyl group, said X having up to 12 non-hydrogen atoms.

5. A metal complex according to claim 1, corresponding to the formula:

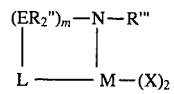

wherein:
E is independently each occurrence silicon or carbon;
R" is independently each occurrence hydrogen or $C_{1-10}$ hydrocarbyl;
R'" is an aryl, benzyl, hydrocarbyl substituted aryl, hydrocarbyl substituted benzyl, secondary or tertiary alkyl or tertiary silyl group of up to 12 nonhydrogen atoms;
M is titanium in the +4 formal oxidation state;
m is an integer from 1 to 3;
L is a (2,4-disubstituted pentadien-3-yl), (2,4-disubstituted pentadien-1-yl), (1,5-disubstituted pentadien-3-yl), (6,6-disubstituted-$\eta^5$-cyclohexadien-3-yl), (6,6-disubstituted-$\eta^5$-cyclosilahexadien-3-yl), (1,2,3,4,5-$\eta$-cyclohexadien-6-yl), (6-substituted-1, 2, 3, 4, 5-$\eta$-cyclohexadien-6-yl), (1,2, 4, 5, 6,6-hexasubstituted-$\eta^5$-cyclohexadien-3-yl)-, (1, 1-disubstituted-$\eta^5$-hexahydronaphthalen-4-yl), (1, 1, 2, 3-tetrasubstituted-$\eta^5$-hexahydronaphthalen-4-yl), or (9, 9-disubstituted-10, 11, 12, 13, 14-$\eta$-1,2, 3, 4, 5, 6, 7, 8, 9, 10-decahydroanthracene-10-yl), said substituents independently each occurrence being hydrocarbyl, silyl, or a mixture thereof of up to 10 nonhydrogen atoms each; and X is methyl, allyl, phenyl, benzyl, chloro,2-(N,N-dimethylamino)benzyl or trimethylsilylmethyl.

6. A metal complex according to claim 5 selected from the group consisting of (tert-butylamido)(dimethyl)($\eta^5$-pentadien-3-yl)silanetitanium dichloride, (tert-butylamido)(dimethyl)($\eta^5$-pentadien-3-yl)silanetitanium dimethyl, (tert-butylamido)(dimethyl)(2,4-dimethyl-$\eta^5$-pentadien-3-yl)silanetitanium dichloride, (tert-butylamido)(dimethyl)(2, 4-dimethyl-$\eta^5$-pentadien-3-yl)silanetitanium dimethyl, (tert-butylamido)(dimethyl)($\eta^5$-pentadien-3-yl)silanezirconium dichloride, (tert-butylamido)(dimethyl)($\eta^5$-pentadien-1-yl)silanezirconium dimethyl, (tert-butylamido)(dimethyl)(2,4-dimethyl-$\eta^5$-pentadien-3-yl)silanezirconium dichloride, (tert-butylamido)(dimethyl)( 2,4-dimethyl-$\eta^5$-pentadien-3-yl)silanezirconium dimethyl, (tert-butylamido)(dimethyl)(1,5-bis(trimethylsilyl)-2,4-dimethyl-$\eta^5$-pentadien- 3-yl)silanetitanium dichloride, (tert-butylamido)(dimethyl)(1,5-bis(trimethylsilyl)- 2,4-dimethyl-η⁵-pentadien-3-yl)silanetitanium dimethyl, (tert-butylamido)(dimethyl)(1,5-bis(trimethylsilyl)-2,4-dimethyl-η⁵-pentadien- 3-yl)silanezirconium dichloride, (tert-butylamido)(dimethyl)(1,5-bis(trimethylsilyl)- 2,4-dimethyl-η⁵-pentadien-3-yl)silanezirconium dimethyl, (tert-butylamido)(dimethyl)(6,6-dimethyl-η⁵-cyclohexadien-3-yl)silanetitanium dichloride, (tert-butylamido)(dimethyl)(6,6-dimethyl-η⁵-cyclohexadien-3-yl)silanetitanium dimethyl, (tert-butylamido)(dimethyl)(6,6-dimethyl-η⁵-cyclosilahexadien-3-yl)silanetitanium dichloride, (tert-butylamido)(dimethyl)( 6,6-dimethyl-η⁵-cyclosilahexadien-3-yl)silanetitanium dimethyl, (tert-butylamido)(dimethyl)(6,6-dimethyl-η⁵-cyclohexadien-3-yl)silanezirconium dichloride, (tert-butylamido)(dimethyl)(6,6-dimethyl-η⁵-cyclohexadien-3-yl)silanezirconium dimethyl, (tert-butylamido)(dimethyl)(6,6-dimethyl-η⁵-cyclosilahexadien- 3-yl)silanezirconium dichloride, (tert-butylamido)(dimethyl)( 6,6-dimethyl-η⁵-cyclosilahexadien-3-yl)silanezirconium dimethyl, (N-tert-butylamido)(dimethyl)(2, 3, 4, 9, 10-η-1, 2-dihydronaphthalen-4-yl)silanetitanium (IV) dimethyl, (N-tert-butylamido)(dimethyl)( 1, 1-dimethyl-2, 3, 4, 9, 10-η-1,4-dihydronaphthalen-4-yl)silanetitanium (IV) dimethyl, (N-tert-butylamido)(dimethyl)(2, 3, 4, 9, 10-η- 1,2, 5, 6, 7, 8-hexahydronaphthalen-4-yl)silanetitanium (IV) dimethyl, (N-tert-butylamido)(dimethyl)( 1,1-dimethyl-2, 3, 4, 9, 10-η-1,2, 5, 6, 7, 8-hexahydronaphthalen-4-yl)silanetitanium (IV) dimethyl, (N-tert-butylamido)(dimethyl)(9, 9-dimethyl-10, 11, 12, 13, 14-η-9,10-dihydroanthracen-10-yl)silanetitanium (IV) dimethyl, (N-tert-butylamido)(dimethyl)(9,9-dimethyl-10, 11, 12, 13, 14-η-1, 2, 3, 4, 9,10-hexahydroanthracen-10-yl)silanetitanium (IV) dimethyl, (N-tert-butylamido)(dimethyl)( 9, 9-dimethyl-10, 11, 12, 13, 14-η-1, 2, 3, 4, 5, 6, 7, 8, 9, 10-decahydroanthracen-10-yl)silanetitanium (IV) dimethyl, and (N-tert-butylamido)(dimethyl)( 9, 9-dimethyl-10, 11, 12, 13, 14-η-1, 2, 3, 4, 5, 6, 7, 8, 9,11-decahydroanthracen-10-yl)silanetitanium (IV) dimethyl.

7. A metal complex according to claim 1 wherein M is in the +2 formal oxidation state.

8. A metal complex according to claim 1 wherein M is in the +4 formal oxidation state.

9. A cationic metal complex corresponding to the formula:

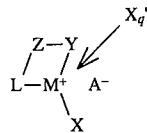

wherein:

M is a Group 4 metal in the +4 formal oxidation state;

L is a group containing a cyclic or noncyclic, non-aromatic, anionic, dienyl ligand group bound to M and Z, said L group containing up to 60 nonhydrogen atoms;

Z is a moiety covalently bound to both L and Y, comprising boron, or a member of Group 14 of the Periodic Table of the Elements, said moiety having up to 60 non-hydrogen atoms;

Y is a moiety comprising nitrogen, phosphorus, sulfur or oxygen through which Y is covalently bound to both Z and M, said moiety having up to 20 nonhydrogen atoms;

X' independently each occurrence is a Lewis base containing up to 40 nonhydrogen atoms;

X independently each occurrence is a monovalent anionic moiety having up to 20 non-hydrogen atoms, provided however that X is not an aromatic group that is π-bonded to M; and q is a number from 0 to 3; and A– is a noncoordinating anion.

10. A metal complex according to claim 9 wherein A⁻ is $B(C_6F_5)_4^-$ or $XB(C_6F_5)_3$ wherein X is $C_{1-10}$ hydrocarbyl.

11. A zwitterionic metal complex corresponding to the formula:

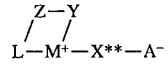

wherein:

M is a Group 4 metal in the +4 oxidation state;

L is a group containing a cyclic or noncyclic, non-aromatic, anionic, dienyl ligand group bound to M and Z, said L group containing up to 60 nonhydrogen atoms;

Z is a moiety covalently bound to both L and Y, comprising boron, or a member of Group 14 of the Periodic Table of the Elements, said moiety having up to 60 non-hydrogen atoms;

Y is a moiety comprising nitrogen, phosphorus, sulfur or oxygen through which Y is covalently bound to both Z and M, said moiety having up to 20 nonhydrogen atoms;

X** is the divalent remnant of a conjugated diene; and

A– is the moiety derived from a neutral Lewis acid activating cocatalyst.

12. A zwitterionic metal complex according to claim 11 wherein A⁻ is $B(C_6F_5)_3^-$.

* * * * *